US011395774B2

(12) United States Patent
Skinner et al.

(10) Patent No.: US 11,395,774 B2
(45) Date of Patent: Jul. 26, 2022

(54) TECHNOLOGIES FOR INCONTINENCE AND MENSTRUAL GARMENTS AND UNDERWEAR

(71) Applicant: Thinx Inc., New York, NY (US)

(72) Inventors: Shama Amalean Skinner, Brooklyn, NY (US); Courtney L. Newman, Woodside, NY (US)

(73) Assignee: Thinx Inc., New York, NY (US)

( * ) Notice: Subject to any disclaimer, the term of this patent is extended or adjusted under 35 U.S.C. 154(b) by 0 days.

(21) Appl. No.: 17/351,033

(22) Filed: Jun. 17, 2021

(65) Prior Publication Data

US 2021/0393454 A1 Dec. 23, 2021

Related U.S. Application Data

(60) Provisional application No. 63/041,509, filed on Jun. 19, 2020.

(51) Int. Cl.
*A61F 13/15* (2006.01)
*A61F 13/539* (2006.01)
(Continued)

(52) U.S. Cl.
CPC .......... *A61F 13/539* (2013.01); *A61F 13/47* (2013.01); *A61F 13/51* (2013.01)

(58) Field of Classification Search
CPC ......... A61F 13/539; A61F 13/47; A61F 13/51
(Continued)

(56) References Cited

U.S. PATENT DOCUMENTS 3,608,551 A 9/1971 Seijo
4,205,679 A 6/1980 Repke et al.
(Continued)

FOREIGN PATENT DOCUMENTS

CA 2126280 12/1994
CA 2126281 12/1994
(Continued)

OTHER PUBLICATIONS

Boys washable absorbent briefs, downloaded from internet Aug. 26, 2019, https://bedwettingstore.com/products/boys~washable~absorbent~briefs~1 (2 pages).
(Continued)

*Primary Examiner* — Jacqueline F Stephens
(74) *Attorney, Agent, or Firm* — Dentons US LLP

(57) ABSTRACT

An absorptive or incontinence and menstrual underwear or garment including a crotch area hosting a stitching, a first layer, a second layer, a third layer, a fourth layer, a fifth layer, a sixth layer, and a seventh layer, wherein the first layer is innermost, wherein the seventh layer is outermost, wherein the second layer extends between the first layer and the third layer, wherein the fourth layer extends between the third layer and the fifth layer, wherein the sixth layer extends between the fifth layer and the seventh layer, wherein the stitching extends through the first layer, the sixth layer, and the seventh layer, wherein the stitching avoids extending through the second layer, the third layer, the fourth layer, and the fifth layer, wherein the second layer is bonded or adhered to the third layer.

30 Claims, 21 Drawing Sheets

(51) Int. Cl.
*A61F 13/51* (2006.01)
*A61F 13/47* (2006.01)

(58) Field of Classification Search
USPC .......................... 604/396, 385.14, 393, 394
See application file for complete search history.

(56) References Cited

U.S. PATENT DOCUMENTS

| | | | |
|---|---|---|---|
| 4,573,987 | A | 3/1986 | Lamb, Jr. |
| 4,641,381 | A | 2/1987 | Heran et al. |
| 4,813,950 | A | 3/1989 | Branch |
| 5,291,617 | A | 3/1994 | Moretz et al. |
| 5,546,607 | A | 8/1996 | Roberts |
| 5,562,648 | A | 10/1996 | Peterson |
| 5,669,902 | A | 9/1997 | Sivilich |
| 5,677,028 | A | 10/1997 | Ravella |
| 5,683,373 | A | 11/1997 | Darby |
| 5,879,487 | A | 3/1999 | Ravella |
| 6,381,994 | B1 | 5/2002 | Lee |
| 6,610,901 | B2 | 8/2003 | McMahon-Ayerst et al. |
| 6,848,121 | B1 | 2/2005 | Halid |
| 6,861,520 | B1 | 3/2005 | Todd et al. |
| 7,008,887 | B2 | 3/2006 | Rearick et al. |
| 7,166,095 | B1 | 1/2007 | Coates |
| 7,842,625 | B1 | 11/2010 | Stockton et al. |
| 7,951,128 | B1 | 5/2011 | Lewis |
| 8,117,675 | B2 | 2/2012 | Strange et al. |
| D701,018 | S | 3/2014 | Wexler |
| 8,935,813 | B2 | 1/2015 | O'Leary |
| 9,011,403 | B2 | 4/2015 | De Bruin et al. |
| 10,342,266 | B2 | 7/2019 | Oh |
| 10,441,479 | B2 | 10/2019 | Griffiths |
| 10,441,480 | B2 | 10/2019 | Griffiths |
| 10,897,941 | B1 | 1/2021 | Smoter |
| 11,207,225 | B2 | 12/2021 | Kajanthan et al. |
| 2005/0055002 | A1 | 3/2005 | Whitelaw et al. |
| 2005/0090795 | A1 | 4/2005 | Coleman |
| 2008/0114327 | A1 | 5/2008 | Barge |
| 2008/0222781 | A1 | 9/2008 | Rhew |
| 2008/0275415 | A1 | 11/2008 | Wheeler et al. |
| 2008/0276352 | A1 | 11/2008 | Strange et al. |
| 2009/0082749 | A1 | 3/2009 | Scott et al. |
| 2010/0249736 | A1 | 9/2010 | Png et al. |
| 2011/0172621 | A1 | 7/2011 | Lee et al. |
| 2012/0071849 | A1 | 3/2012 | Kumar |
| 2012/0180198 | A1 | 7/2012 | Ruggieri |
| 2013/0041339 | A1 | 2/2013 | Taylor |
| 2013/0046265 | A1 | 2/2013 | Felix |
| 2013/0072888 | A1 | 3/2013 | Zorin |
| 2014/0018756 | A1 | 1/2014 | De Bruin et al. |
| 2014/0025027 | A1 | 1/2014 | Png et al. |
| 2014/0039432 | A1* | 2/2014 | Dunbar ............. A61F 13/15577 604/360 |
| 2016/0089276 | A1 | 3/2016 | Griffiths |
| 2016/0112695 | A1 | 4/2016 | Kim |
| 2018/0014983 | A1 | 1/2018 | Jayasuriya et al. |
| 2018/0092787 | A1 | 4/2018 | Griffiths |
| 2021/0030605 | A1 | 2/2021 | Kajanthan et al. |
| 2021/0282469 | A1 | 9/2021 | Siriwardena |

FOREIGN PATENT DOCUMENTS

| | | |
|---|---|---|
| DE | 202004019377 U1 | 2/2005 |
| EP | 0619953 | 10/1994 |
| EP | 2879534 | 3/2017 |
| GB | 2130076 A | 5/1984 |
| JP | 2005111181 A | 4/2005 |
| JP | 3718213 B1 | 11/2005 |
| KR | 100694187 | 3/2007 |
| WO | WO2006073719 | 7/2006 |
| WO | WO2010111717 | 9/2010 |
| WO | WO2014026236 | 2/2014 |
| WO | WO2016133458 | 8/2016 |
| WO | WO2021/112695 | 6/2021 |

OTHER PUBLICATIONS

Bruce Medical Supply, Hi-Cut Stay-Dry Briefs, downloaded from internet Jun. 21, 2021, https://www.brucemedical.com/hicstaybrief.html (1 pages).

Bryn, Finally, Some Oops-Free Underwear: Thank You OnGossamer Luxury Liner, downloaded from internet Jun. 21, 2021, http://www.shefinds.com/2008/finally_some_oops_free_underwear_thank_you_ongossamer_luxury_liner/# (1 page).

Hinde, These Period Pants Stop Leaks So Women Can Get On Wth Their Lives Whether It's That Time Of The Month Or Not, The Huffington Post UK, Mar. 6, 2015, downloaded from internet Jun. 21, 2021, https://www.huffingtonpost.co.uk/2015/06/03/period-pants-thinx-invention_n_7499906.html (8 pages).

International Search Report dated Jul. 25, 2014 for PCT/CA2014/000389 filed May 2, 2014 (7 pages).

Johnson, Can These Panties Disrupt the $15 Billion Feminine Hygiene Market?, Forbes, May 28, 2015, Downloaded from internet Jun. 21, 2021, https://www.forbes.com/sites/emmajohnson/2015/05/28/can-these-panties-disrupt-a-15-billion-feminine-hygiene-market/?sh=176f7ddc3c5e (7 pages).

Kylie incontinence briefs, downloaded from internet Aug. 26, 2019, https://www.win-health.com/kylie-absorbent-incontinence-briefs.html (3 pages).

Noman, Three Feminist Geniuses Just Invented a Pair of Panties That Could Change the World, Jun. 1, 2014, downloaded from internet Jun. 21, 2021, https://www.mic.com/articles/119796/this~new~magic~underwear~means~you~never~have~to~use~tampons~or~pads~again (6 pages).

International Search Report dated Sep. 27, 2021 for PCT/US2021/037927 filed Jun. 17, 2021 (13 pages).

* cited by examiner

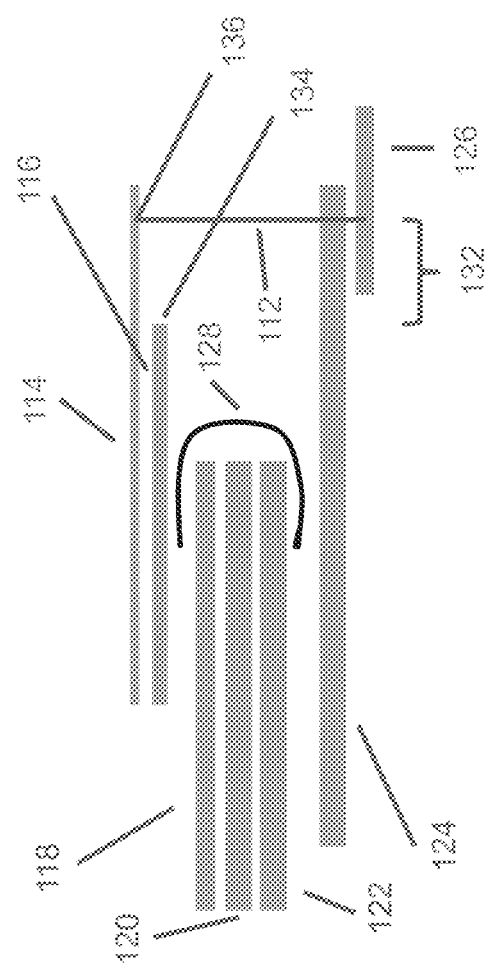

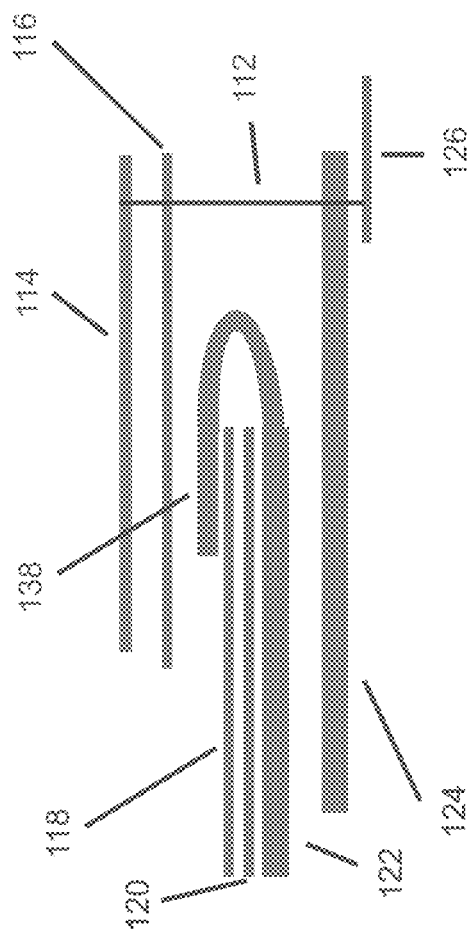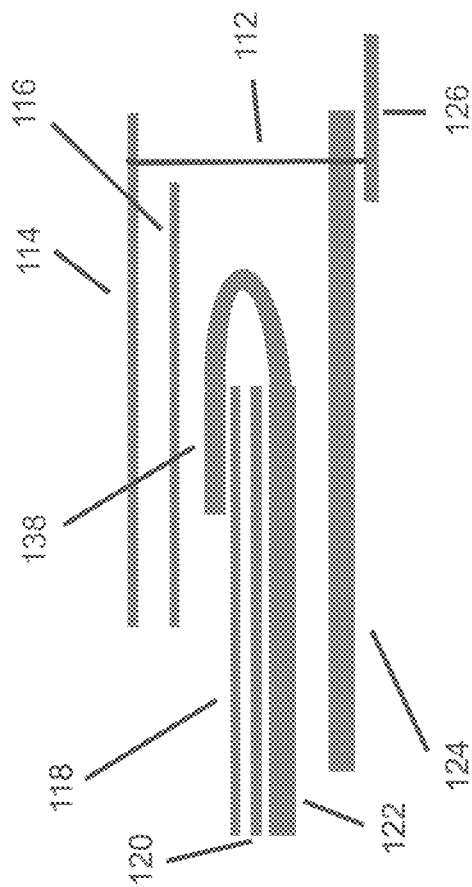

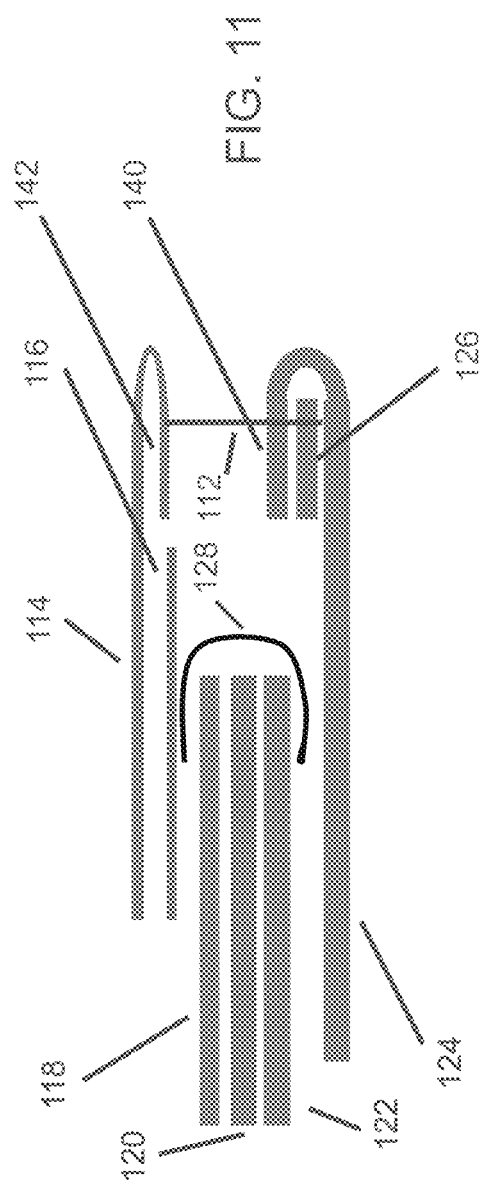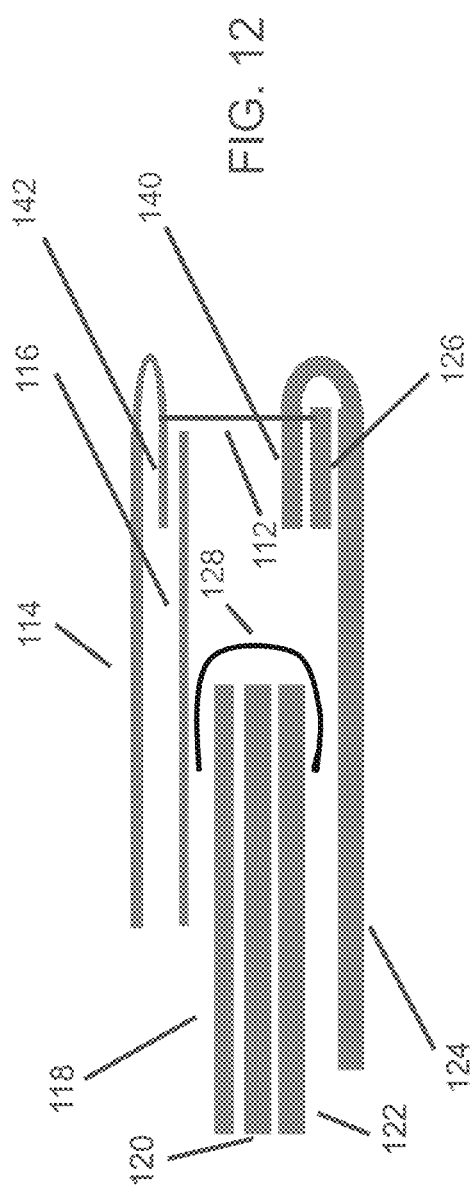

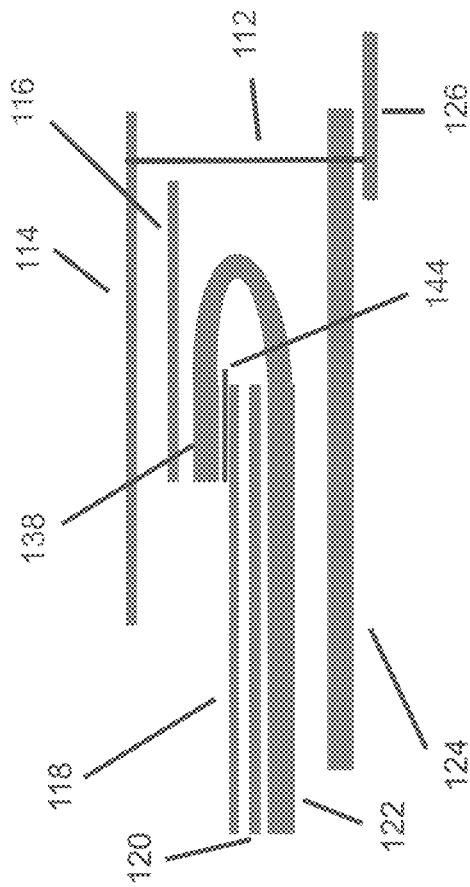
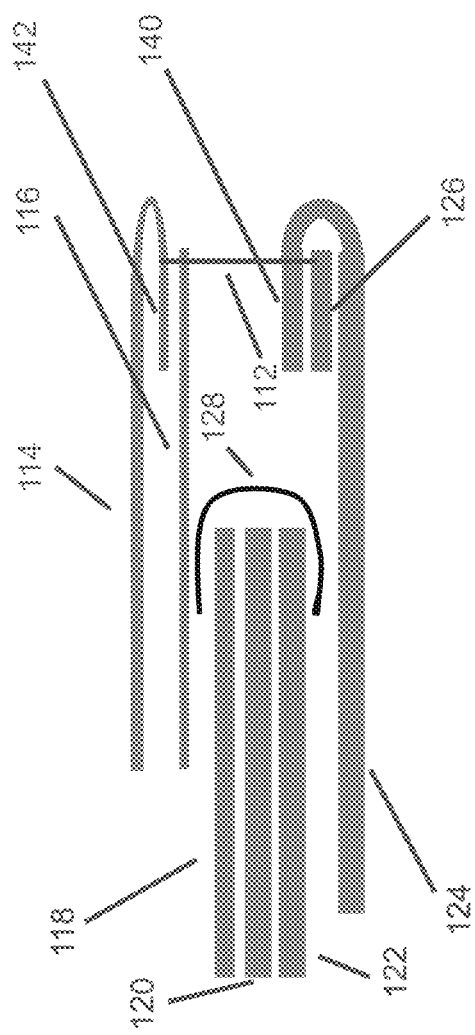

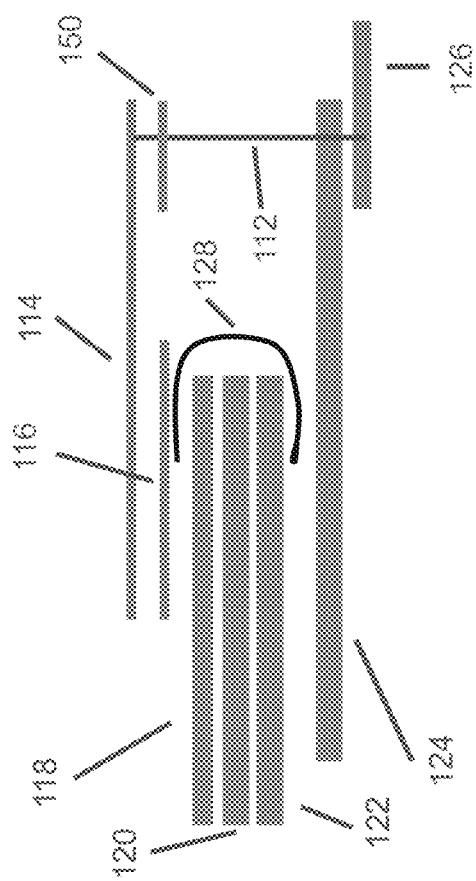
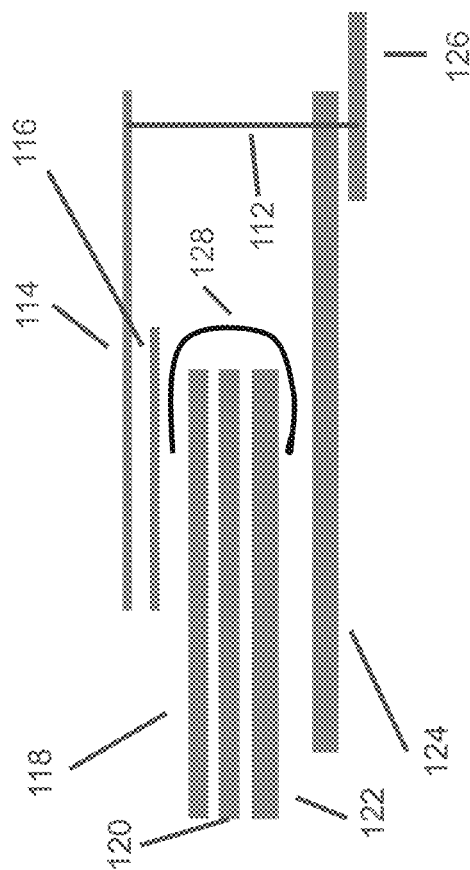

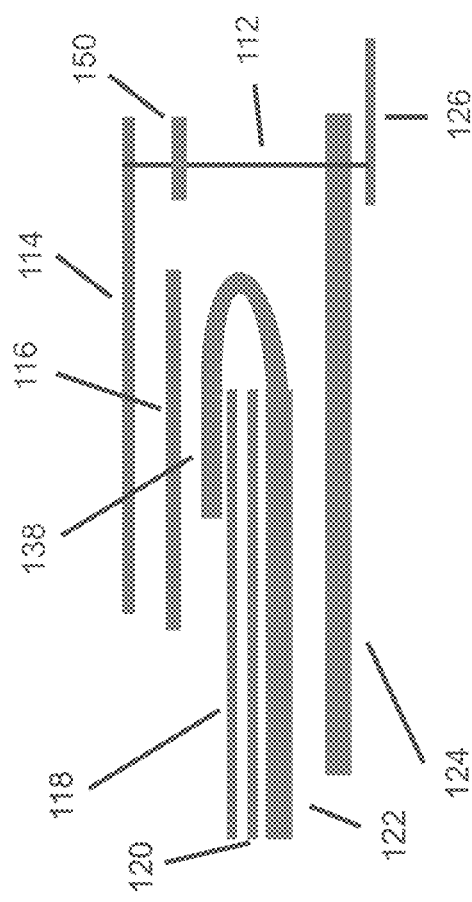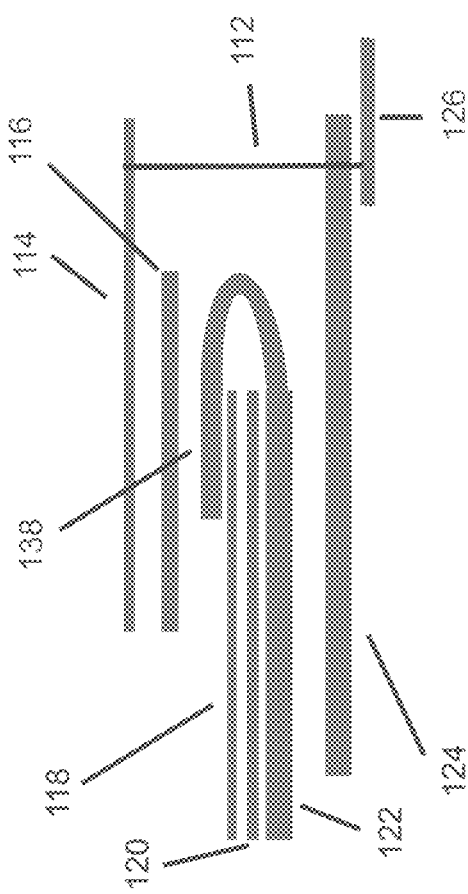

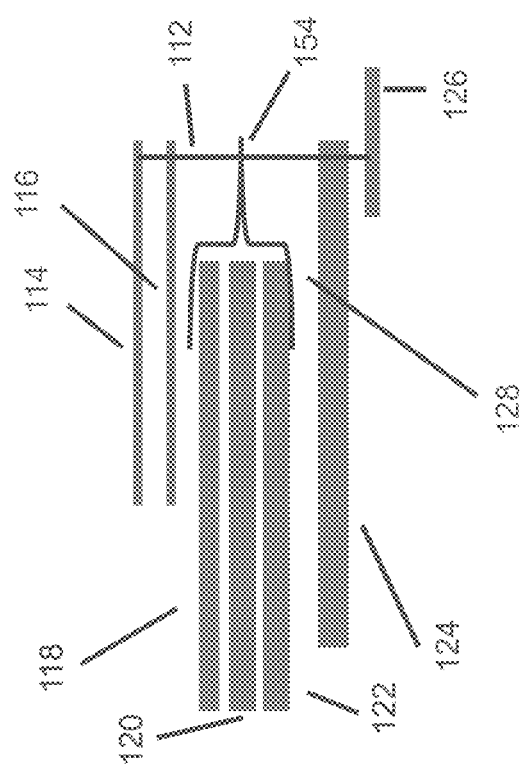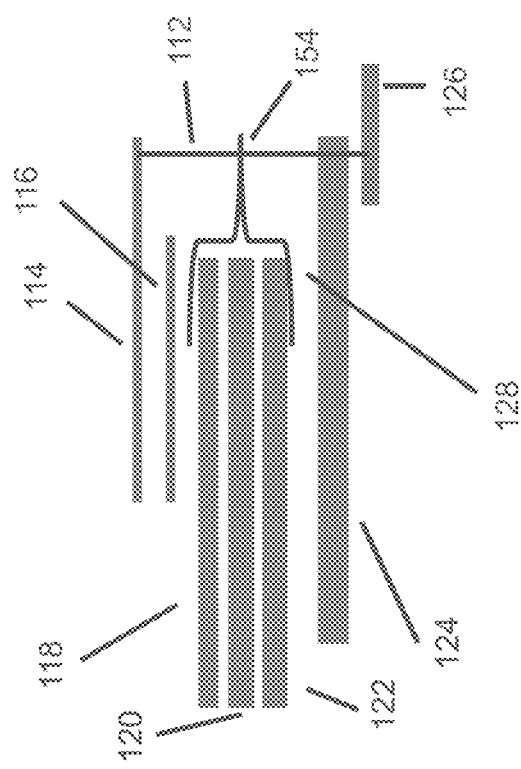

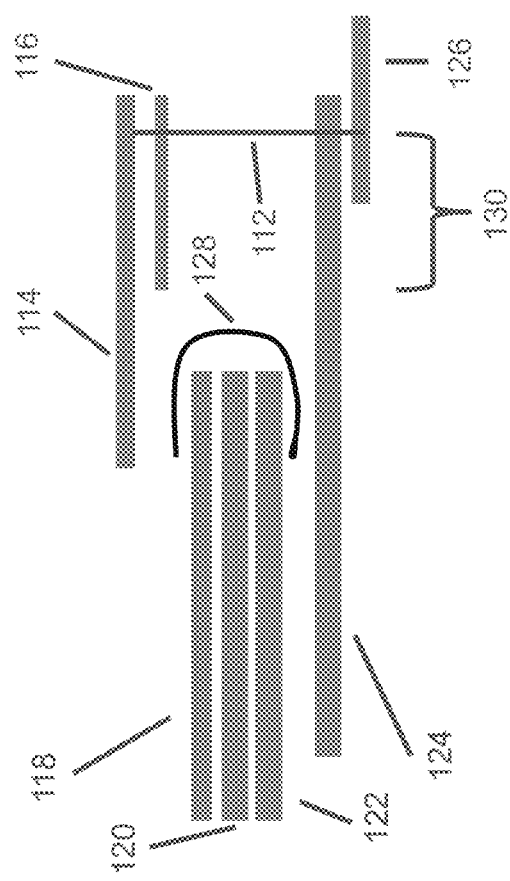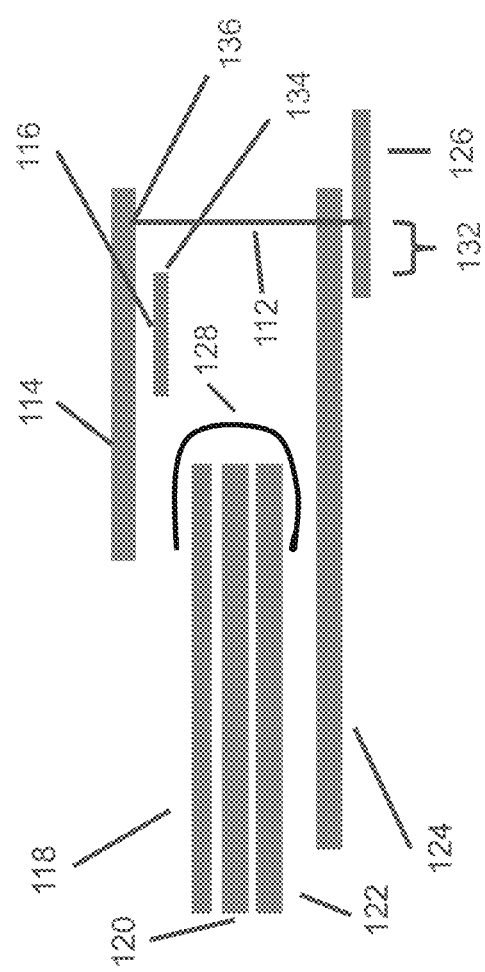

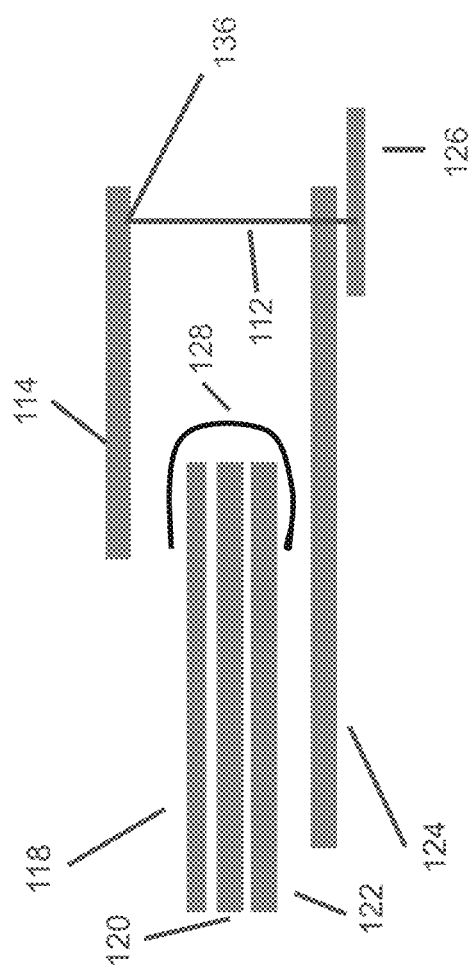

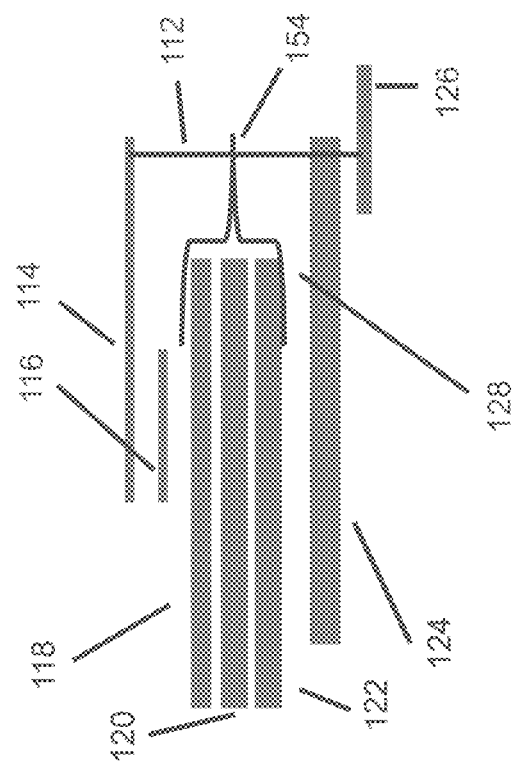
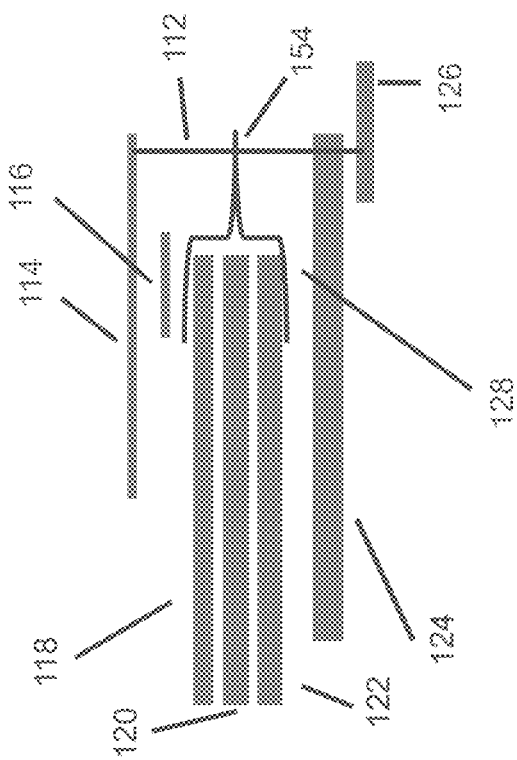

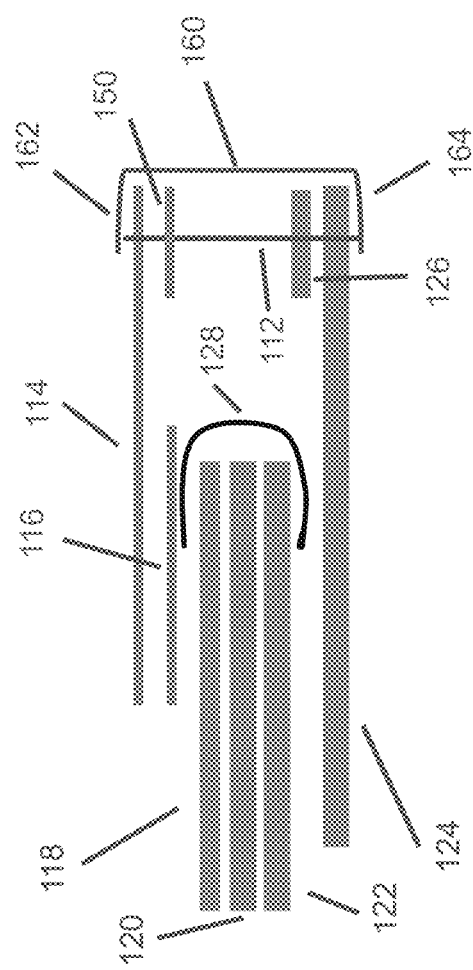
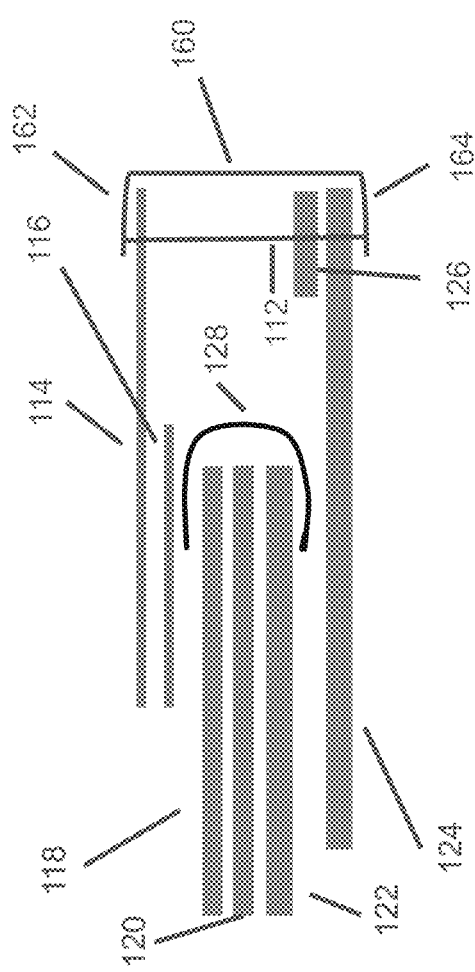

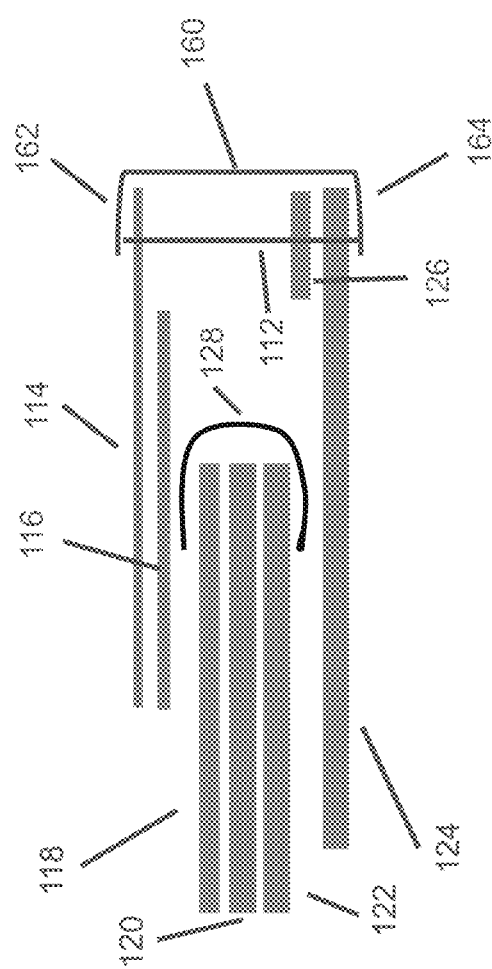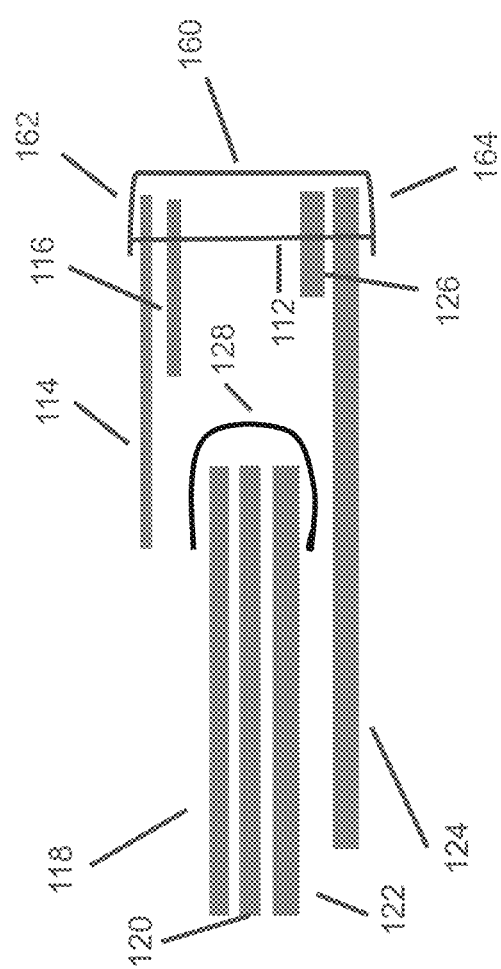

TECHNOLOGIES FOR INCONTINENCE AND MENSTRUAL GARMENTS AND UNDERWEAR

CROSS REFERENCE

This application claims the benefit of U.S. Provisional Patent Application 63/041,509 filed 19 Jun. 2020; which is incorporated by reference herein in its entirety for all purposes.

TECHNICAL FIELD

This disclosure relates to absorptive garments and underwear, including incontinence and menstrual underwear and garments.

BACKGROUND

In this disclosure, where a document, an act, and/or an item of knowledge is referred to and/or discussed, then such reference and/or discussion is not an admission that the document, the act, and/or the item of knowledge and/or any combination thereof was at a priority date, publicly available, known to a public, part of common general knowledge, and/or otherwise constitutes any prior art under any applicable statutory provisions; and/or is known to be relevant to any attempt to solve any problem with which this disclosure is concerned with. Further, nothing is disclaimed.

There is a desire to enable an incontinence and menstrual underwear and garment that is sufficiently waterproof, yet adequately resistant to wear and tear. However, despite various attempts by others, this type of absorptive or incontinence and menstrual underwear or garment does not yet exist.

SUMMARY

This disclosure enables an absorptive or incontinence and menstrual underwear and garment that is sufficiently waterproof, yet adequately resistant to wear and tear. This disclosure at least partially addresses at least one of above inefficiencies. However, this disclosure can prove useful to other technical areas. Therefore, various claims recited below should not be construed as necessarily limited to addressing any of the above inefficiencies.

According to an embodiment of this disclosure, a device comprises: an absorptive or incontinence and menstrual underwear or garment including a crotch area hosting a stitching, a first layer, a second layer, a third layer, a fourth layer, a fifth layer, a sixth layer, and a seventh layer, wherein the first layer is innermost, wherein the seventh layer is outermost, wherein the second layer extends between the first layer and the third layer, wherein the fourth layer extends between the third layer and the fifth layer, wherein the sixth layer extends below the fifth layer and above the seventh layer, wherein the stitching extends through the first layer, the sixth layer, and the seventh layer, wherein the stitching avoids extending through the second layer, the third layer, the fourth layer, and the fifth layer, wherein the second layer is bonded or adhered to the third layer.

The device according to one of the prior embodiments, wherein the second layer is adhered or bonded to the first layer.

The device according to one of the prior embodiments, wherein the second layer is adhered or bonded to the sixth layer.

The device according to one of the prior embodiments, wherein the first layer is coupled to the sixth layer via the second layer.

The device according to one of the prior embodiments, wherein a material extends from below the fifth layer to above the third layer. The device according to one of the prior embodiments, wherein the material is coupled to the bottom of the fifth layer and to the top of the third layer. The device according to one of the prior embodiments, wherein the material is coupled to the bottom of the second layer. The device according to one of the prior embodiments, wherein the material is coupled to the bottom of the first layer.

The device according to one of the prior embodiments, wherein the second layer extends over a portion of the sixth layer but not over the third layer.

The device according to one of the prior embodiments, wherein the material extends over the third layer and under the first layer but not under the second layer.

The device according to one of the prior embodiments, wherein the second layer extends under the first layer and over the third layer and over the material, but not over the sixth layer. The device according to one of the prior embodiments, wherein the material is a bonding strip.

The device according to one of the prior embodiments, wherein the sixth layer has a first portion and a second portion and wherein the first portion of the sixth layer extend below the seventh layer and the second portion of the sixth layer extends above the seventh layer.

The device according to an embodiment, wherein the stitching extends through the second portion of the sixth layer but not through the first portion of the sixth layer.

The device according to an embodiment, wherein the stitching extends through the second portion of the sixth layer and through the seventh layer but not through the first portion of the sixth layer.

The device according to one of the prior embodiments, wherein the second portion of the sixth layer extends below the first layer.

The device according to one of the prior embodiments, wherein the second portion of the sixth layer extends below the first layer and the second layer.

The device according to one of the prior embodiments, wherein the first layer has a first portion and a second portion and wherein the second portion of the first layer extend below the first portion of the first layer and wherein the stitching extends through the second portion of the first layer but not through the first portion of the first layer.

The device according to one of the prior embodiments, wherein the first layer has a first portion and a second portion and wherein the second portion of the first layer extend below the first portion of the first layer, wherein the sixth layer has a first portion and a second portion and wherein the first portion of the sixth layer extend below the seventh layer and the second portion of the sixth layer extends above the seventh layer, and wherein the stitching extends through the second portion of the first layer but not through the first portion of the first layer, through the second portion of the sixth layer but not through the first portion of the sixth layer, and through the seventh layer.

The device according to one of the prior embodiments, further comprising a material, such as, for example, a bonding strip, that extends from below the fifth layer to above the third layer along the entire peripheries of the third layer, the fourth layer and the fifth layer.

The device according to one of the prior embodiments, wherein an edge of the fifth layer extends above the third layer along the entire peripheries of the third layer and the fourth layer and wherein the edge of the fifth layer is coupled to a top portion of the third layer. The device according to one of the prior embodiments, wherein the edge of the fifth layer is bonded to the third layer using a bonding strip. The device according to one of the prior embodiments, wherein the second layer extends over the third layer and the edge of the fifth layer but not over the sixth layer. The device according to one of the prior embodiments, wherein the material, such as, for example, a piece of bonding strip, is positioned under the first layer and over the sixth layer but does not extend over the second layer, under the second layer, over the edge of the fifth layer or over the third layer.

The device according to one of the prior embodiments, wherein the material, such as, for example, a bonding strip, includes an end portion that extends over the sixth layer and under the second layer, and wherein the stitching extends through the first layer, the second layer, the end portion of the material, the sixth layer and the seventh layer.

The device according to one of the prior embodiments, wherein the material, such as, for example, a bonding strip, includes an end portion that extends over the sixth layer and under the first layer but not under the second layer, and wherein the stitching extends through the first layer, the end portion of the material, the sixth layer and the seventh layer.

The device according to one of the prior embodiments, wherein the first layer extends over the material, such as, for example, a bonding strip, over the sixth layer and over the second layer, wherein the second layer extends over the sixth layer and under the first layer, and wherein the stitching extends through the first layer, the second layer, the sixth layer and the seventh layer, and wherein the second layer is coupled to the first layer and the sixth layer and the first layer is coupled to the material.

The device according to one of the prior embodiments, wherein the first layer extends over the material, such as, for example, a bonding strip, over the sixth layer and over the second layer, wherein the second layer extends over the sixth layer and under the first layer, and wherein the stitching extends through the first layer, the sixth layer and the seventh layer, and wherein the second layer is coupled to the first layer and the sixth layer and the first layer is coupled to the material.

According to an embodiment of this disclosure, a method comprises: causing an absorptive or incontinence and menstrual underwear or garment to include a crotch area hosting a stitching, a first layer, a second layer, a third layer, a fourth layer, a fifth layer, a sixth layer, and a seventh layer, wherein the first layer is innermost, wherein the seventh layer is outermost, causing the second layer to extend between the first layer and the third layer such that the second layer is bonded or adhered to the third layer; causing the fourth layer to extend between the third layer and the fifth layer; causing the sixth layer to extend below the fifth layer and above the seventh layer; causing the stitching to extend through the first layer, the second layer, the sixth layer, and the seventh layer and avoid extending through the third layer, the fourth layer, and the fifth layer.

According to an embodiment of this disclosure, a method comprises: causing an absorptive or incontinence and menstrual underwear or garment to include a crotch area hosting a stitching, a first layer, a second layer, a third layer, a fourth layer, a fifth layer, a sixth layer, and a seventh layer, wherein the first layer is innermost, wherein the seventh layer is outermost, causing the second layer to extend between the first layer and the third layer such that the second layer is bonded or adhered to the third layer; causing the fourth layer to extend between the third layer and the fifth layer; causing the sixth layer to extend below the fifth layer and above the seventh layer; causing the stitching to extend through the first layer, the sixth layer, and the seventh layer and avoid extending through the second layer, the third layer, the fourth layer, and the fifth layer.

The method according to one of the prior embodiments, wherein the second layer is adhered or bonded to the first layer.

The method according to one of the prior embodiments, wherein the second layer is adhered or bonded to the sixth layer.

The method according to one of the prior embodiments, wherein the first layer is coupled to the sixth layer via the second layer.

The method according to one of the prior embodiments, wherein the sixth layer has a first portion and a second portion and wherein the first portion of the sixth layer extends below the seventh layer and the second portion of the sixth layer extends above the seventh layer.

The method according to an embodiment, wherein the stitching extends through the second portion of the sixth layer but not through the first portion of the sixth layer.

The method according to an embodiment, wherein the stitching extends through the second portion of the sixth layer and through the seventh layer but not through the first portion of the sixth layer.

The method according to one of the prior embodiments, wherein the second portion of the sixth layer extends below the first layer.

The method according to one of the prior embodiments, wherein the second portion of the sixth layer extends below the first layer and the second layer.

The method according to one of the prior embodiments, wherein the first layer has a first portion and a second portion and wherein the second portion of the first layer extend below the first portion of the first layer and wherein the stitching extends through the second portion of the first layer but not through the first portion of the first layer.

The method according to one of the prior embodiments, wherein the first layer has a first portion and a second portion and wherein the second portion of the first layer extends below the first portion of the first layer, wherein the sixth layer has a first portion and a second portion and wherein the first portion of the sixth layer extend below the seventh layer and the second portion of the sixth layer extends above the seventh layer, and wherein the stitching extends through the second portion of the first layer but not through the first portion of the first layer, through the second portion of the sixth layer but not through the first portion of the sixth layer, and through the seventh layer.

The method according to one of the prior embodiments, further comprising coupling a bonding strip that extends from below the fifth layer to above the third layer along the entire peripheries of the third layer, the fourth layer and the fifth layer.

The method according to one of the prior embodiments, wherein an edge of the fifth layer extends above the third layer along the entire peripheries of the third layer and the fourth layer and wherein the edge of the fifth layer is coupled to a top portion of the third layer.

The method according to one of the prior embodiments, wherein the edge of the fifth layer is bonded to the third layer using a bonding strip. The method according to one of the prior embodiments, wherein the second layer extends over the third layer and the edge of the fifth layer but not over the sixth layer. The method according to one of the prior embodiments, wherein the material, such as, for example, a piece of bonding strip, is positioned under the first layer and over the sixth layer but does not extend over the second layer, under the second layer, over the edge of the fifth layer or over the third layer.

The method according to one of the prior embodiments, wherein the material, such as, for example, a bonding strip, includes an end portion that extends over the sixth layer and under the second layer, and wherein the stitching extends through the first layer, the second layer, the end portion of the material, the sixth layer and the seventh layer.

The method according to one of the prior embodiments, wherein the material, such as, for example, a bonding strip, includes an end portion that extends over the sixth layer and under the first layer but not under the second layer, and wherein the stitching extends through the first layer, the end portion of the material, the sixth layer and the seventh layer.

The method according to one of the prior embodiments, wherein the first layer extends over the material, such, for example, a bonding strip, over the sixth layer and over the second layer, wherein the second layer extends over the sixth layer and under the first layer, and wherein the stitching extends through the first layer, the second layer, the sixth layer and the seventh layer, and wherein the second layer is coupled to the first layer and the sixth layer and the first layer is coupled to the material.

The method according to one of the prior embodiments, wherein the first layer extends over the material, such as, for example, a bonding strip, over the sixth layer and over the second layer, wherein the second layer extends over the sixth layer and under the first layer, and wherein the stitching extends through the first layer, the sixth layer and the seventh layer, and wherein the second layer is coupled to the first layer and the sixth layer and the first layer is coupled to the material.

This disclosure is embodied in various forms illustrated in a set of accompanying illustrative drawings. Note that variations are contemplated as being a part of this disclosure, limited only by a scope of various claims recited below.

DESCRIPTION OF DRAWINGS

The set of accompanying illustrative drawings shows various example embodiments of this disclosure. Such drawings are not to be construed as necessarily limiting this disclosure. Like numbers and/or similar numbering scheme can refer to like and/or similar elements throughout.

FIG. 8 shows a cross-sectional view of a crotch area of the incontinence and menstrual underwear or garment according to an embodiment of this disclosure.

FIG. 9 shows a cross-sectional view of a crotch area of the incontinence and menstrual underwear or garment according to an embodiment of this disclosure.

FIG. 10 shows a cross-sectional view of a crotch area of the incontinence and menstrual underwear or garment according to an embodiment of this disclosure.

FIG. 11 shows a cross-sectional view of a crotch area of the incontinence and menstrual underwear or garment according to an embodiment of this disclosure.

FIG. 12 shows a cross-sectional view of a crotch area of the incontinence and menstrual underwear or garment according to an embodiment of this disclosure.

FIG. 13 shows a cross-sectional view of a crotch area of the incontinence and menstrual underwear or garment according to an embodiment of this disclosure.

FIG. 14 shows a cross-sectional view of a crotch area of the incontinence and menstrual underwear or garment according to an embodiment of this disclosure.

FIG. 15 shows a cross-sectional view of a crotch area of the incontinence and menstrual underwear or garment according to an embodiment of this disclosure.

FIG. 16 shows a cross-sectional view of a crotch area of the incontinence and menstrual underwear or garment according to an embodiment of this disclosure.

FIG. 17 shows a cross-sectional view of a crotch area of the incontinence and menstrual underwear or garment according to an embodiment of this disclosure.

FIG. 18 shows a cross-sectional view of a crotch area of the incontinence and menstrual underwear or garment according to an embodiment of this disclosure.

FIG. 21 shows a cross-sectional view of a crotch area of the incontinence and menstrual underwear or garment according to an embodiment of this disclosure.

FIG. 22 shows a cross-sectional view of a crotch area of the incontinence and menstrual underwear or garment according to an embodiment of this disclosure.

FIG. 23 shows a cross-sectional view of a crotch area of the incontinence and menstrual underwear or garment according to an embodiment of this disclosure.

FIG. 24 shows a cross-sectional view of a crotch area of the incontinence and menstrual underwear or garment according to an embodiment of this disclosure.

FIG. 25 shows a cross-sectional view of a crotch area of the incontinence and menstrual underwear or garment according to an embodiment of this disclosure.

FIG. 26 shows a cross-sectional view of a crotch area of the incontinence and menstrual underwear or garment according to an embodiment of this disclosure.

FIG. 27 shows a cross-sectional view of a crotch area of the incontinence and menstrual underwear or garment according to an embodiment of this disclosure.

FIG. 30 shows a cross-sectional view of a crotch area of the incontinence and menstrual underwear or garment according to an embodiment of this disclosure.

FIG. 31 shows a cross-sectional view of a crotch area of the incontinence and menstrual underwear or garment according to an embodiment of this disclosure.

FIG. 32 shows a cross-sectional view of a crotch area of the incontinence and menstrual underwear or garment according to an embodiment of this disclosure.

FIG. 33 shows a cross-sectional view of a crotch area of the incontinence and menstrual underwear or garment according to an embodiment of this disclosure.

DETAILED DESCRIPTION OF PREFERRED EMBODIMENTS

Figure 1:
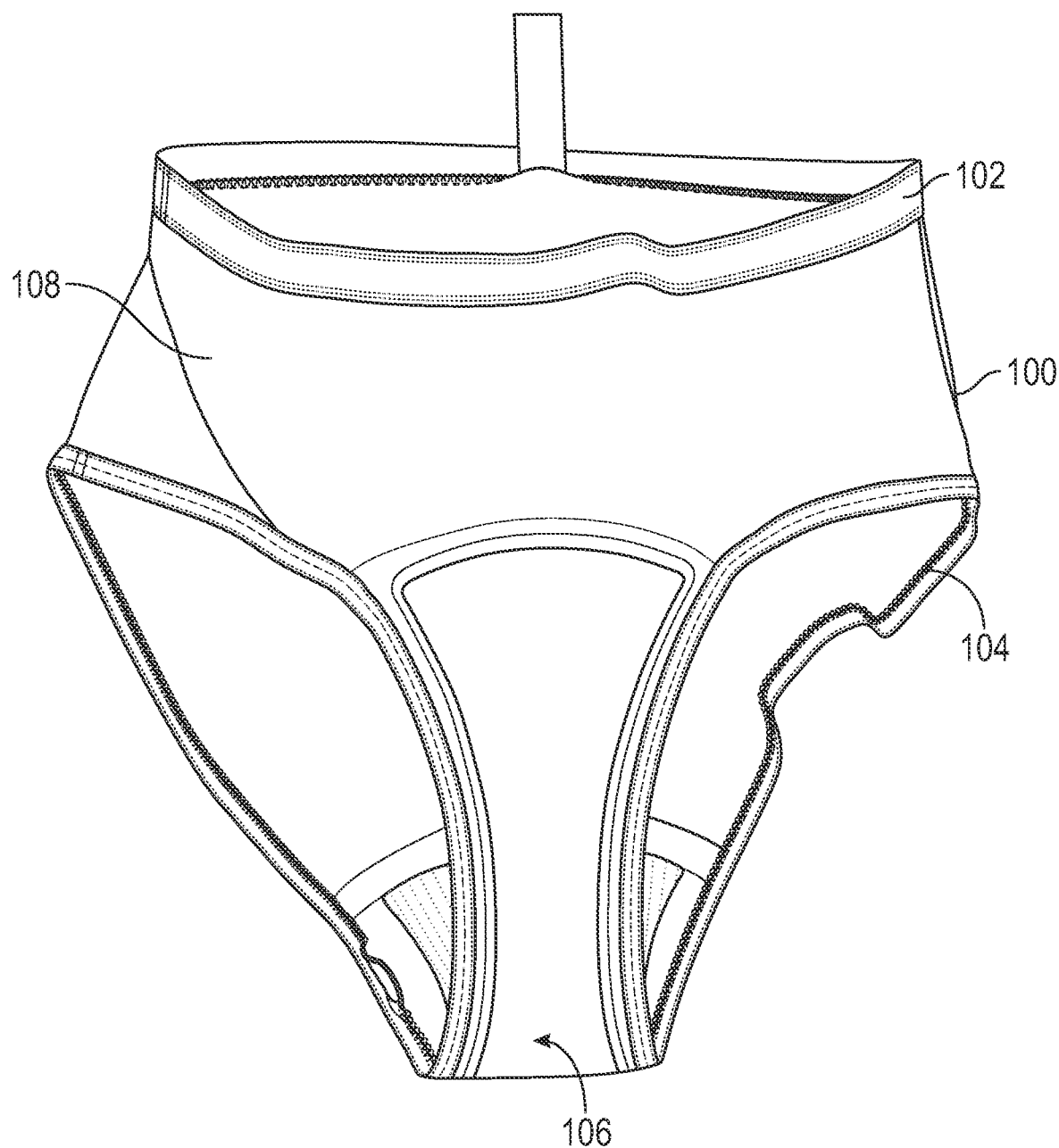
FIGS. 1-7 show various perspective views of an incontinence and menstrual underwear or garment according to this disclosure.

This disclosure is now described more fully with reference to the set of accompanying illustrative drawings, in which example embodiments of this disclosure are shown.

This disclosure can be embodied in many different forms and should not be construed as necessarily being limited to the example embodiments disclosed herein. Rather, the example embodiments are provided so that this disclosure is thorough and complete, and fully conveys various concepts of this disclosure to those skilled in a relevant art.

Features described with respect to certain example embodiments can be combined and sub-combined in and/or with various other example embodiments. Also, different aspects and/or elements of example embodiments, as disclosed herein, can be combined and sub-combined in a similar manner as well. Further, some example embodiments, whether individually and/or collectively, can be components of a larger system, wherein other procedures can take precedence over and/or otherwise modify their application. Additionally, a number of steps can be required before, after, and/or concurrently with example embodiments, as disclosed herein. Note that any and/or all methods and/or processes, at least as disclosed herein, can be at least partially performed via at least one entity in any manner.

Various terminology used herein can imply direct or indirect, full or partial, temporary or permanent, action or inaction. For example, when an element is referred to as being "on," "connected" or "coupled" to another element, then the element can be directly on, connected or coupled to the other element and/or intervening elements can be present, including indirect and/or direct variants. In contrast, when an element is referred to as being "directly connected" or "directly coupled" to another element, there are no intervening elements present.

Although the terms first, second, etc. can be used herein to describe various elements, components, regions, layers and/or sections, these elements, components, regions, layers and/or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Various terminology used herein is for describing particular example embodiments and is not intended to be necessarily limiting of this disclosure. As used herein, various singular forms "a," "an" and "the" are intended to include various plural forms as well, unless a context clearly indicates otherwise. Various terms "comprises," "includes" and/or "comprising," "including" when used in this specification, specify a presence of stated features, integers, steps, operations, elements, and/or components, but do not preclude the presence and/or addition of one or more other features, integers, steps, operations, elements, components, and/or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

Example embodiments of this disclosure are described herein with reference to illustrations of idealized embodiments (and intermediate structures) of this disclosure. As such, variations from various illustrated shapes as a result, for example, of manufacturing techniques and/or tolerances, are to be expected. Thus, various example embodiments of this disclosure should not be construed as necessarily limited to various particular shapes of regions illustrated herein, but are to include deviations in shapes that result, for example, from manufacturing.

Any and/or all elements, as disclosed herein, can be formed from a same, structurally continuous piece, such as being unitary, and/or be separately manufactured and/or connected, such as being an assembly and/or modules. Any and/or all elements, as disclosed herein, can be manufactured via any manufacturing processes, whether additive manufacturing, subtractive manufacturing, and/or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Any and/or all elements, as disclosed herein, can be and/or include, whether partially and/or fully, a solid, including a metal, a mineral, an amorphous material, a ceramic, a glass ceramic, an organic solid, such as wood and/or a polymer, such as rubber, a composite material, a semiconductor, a nanomaterial, a biomaterial and/or any combinations thereof. Any and/or all elements, as disclosed herein, can be and/or include, whether partially and/or fully, a coating, including an informational coating, such as ink, an adhesive coating, a melt-adhesive coating, such as vacuum seal and/or heat seal, a release coating, such as tape liner, a low surface energy coating, an optical coating, such as for tint, color, hue, saturation, tone, shade, transparency, translucency, opaqueness, luminescence, reflection, phosphorescence, anti-reflection and/or holography, a photo-sensitive coating, an electronic and/or thermal property coating, such as for passivity, insulation, resistance or conduction, a magnetic coating, a water-resistant and/or waterproof coating, a scent coating and/or any combinations thereof. Any and/or all elements, as disclosed herein, can be rigid, flexible, and/or any other combinations thereof. Any and/or all elements, as disclosed herein, can be identical and/or different from each other in material, shape, size, color and/or any measurable dimension, such as length, width, height, depth, area, orientation, perimeter, volume, breadth, density, temperature, resistance, and so forth.

Unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized and/or overly formal sense unless expressly so defined herein.

Furthermore, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" and/or "substantially" refers to a +/−10% variation from a nominal value/term. Such variation is always included in any given value/term provided herein, whether or not such variation is specifically referred thereto.

If any disclosures are incorporated herein by reference and such disclosures conflict in part and/or in whole with this disclosure, then to an extent of a conflict, if any, and/or a broader disclosure, and/or broader definition of terms, this disclosure controls. If such disclosures conflict in part and/or in whole with one another, then to an extent of a conflict, if any, a later-dated disclosure controls.

The term "garment" includes without limitation any item that is worn. A garment also includes, without limitation, any item that has a crotch area. A garment includes, for example, an underwear, a brief, an undergarment, a bathing suit, a pajama, a shorts, a leotard, a legging, a pants, a skort, a panty, a boy short, a bikini, a thong, an overalls, a bodysuit, a leotard, a tights, a pantyhose, a boxers, a biking shorts, or a compression shorts.

FIGS. 1-7 show various perspective views of an absorptive or incontinence and menstrual underwear or garment according to this disclosure. FIG. 8 shows a cross-sectional view of a crotch area of the incontinence and menstrual underwear or garment according to this disclosure. In particular, an incontinence and menstrual underwear or garment 100 includes a waistband 102, a front area 108, a back area 110, and a pair of leg openings 104 that define a crotch area 106 therebetween, any of which can include any suitable material (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, tencel).

Figure 2:
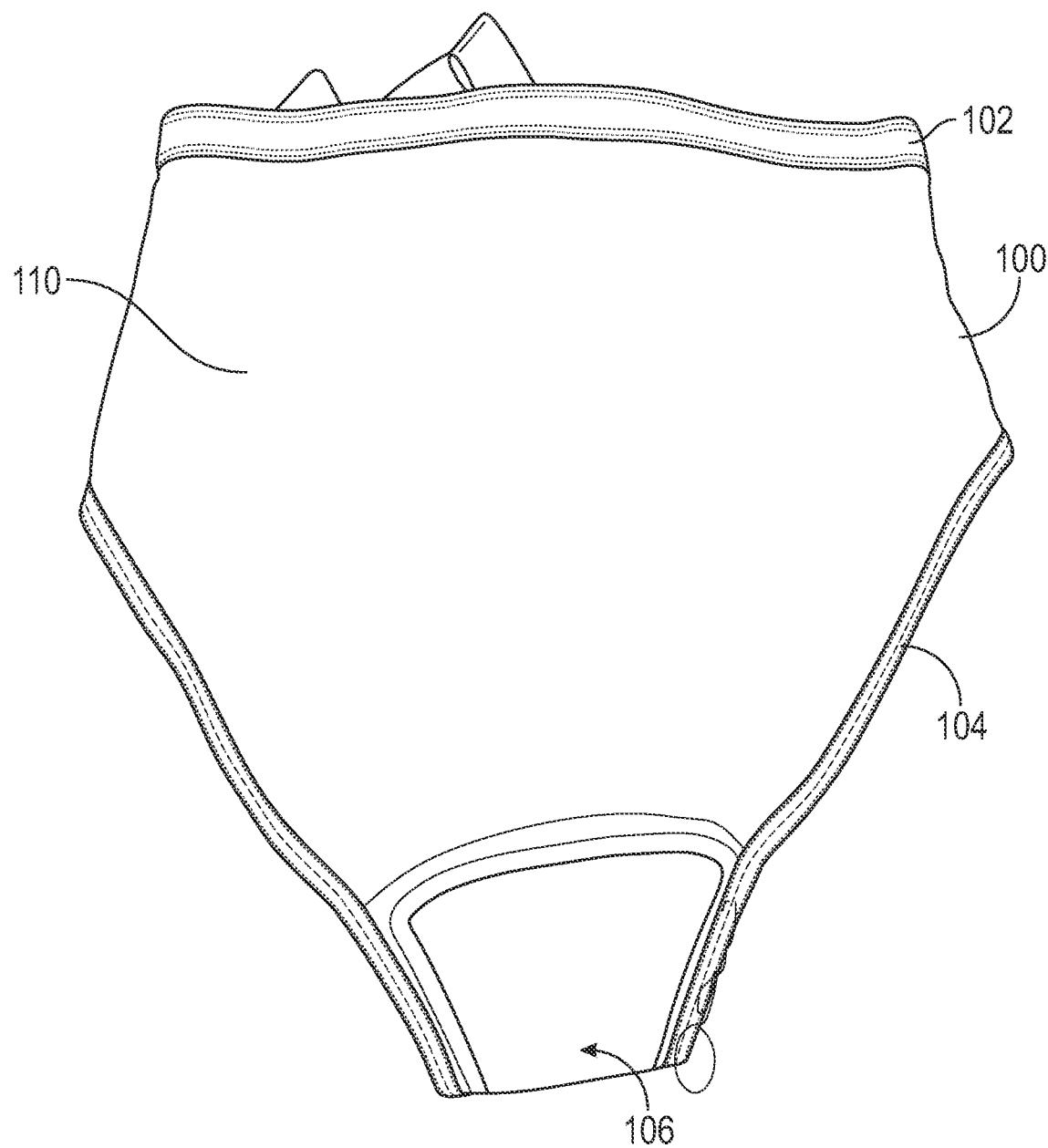
Figure 3:
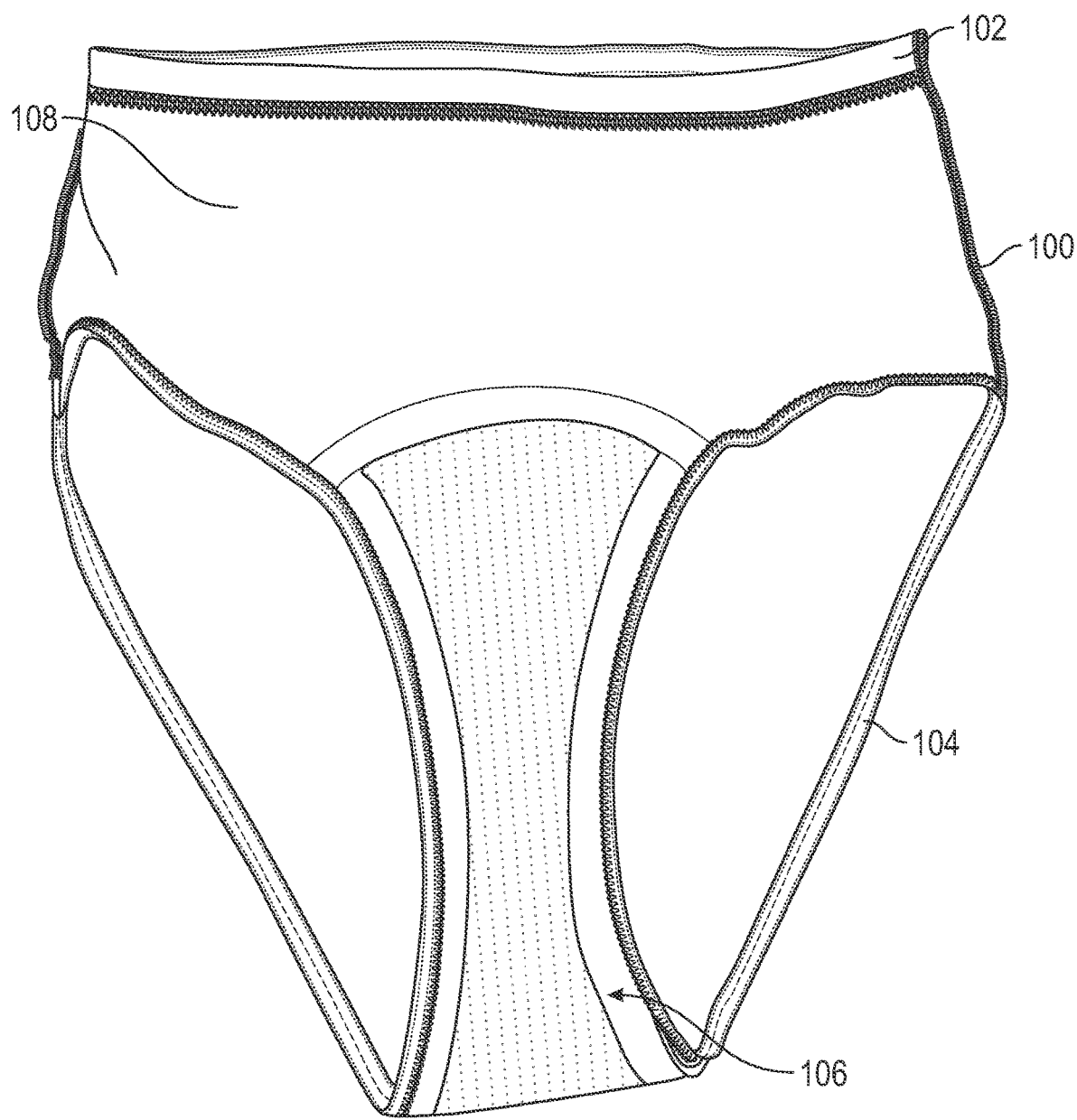
Figure 4:
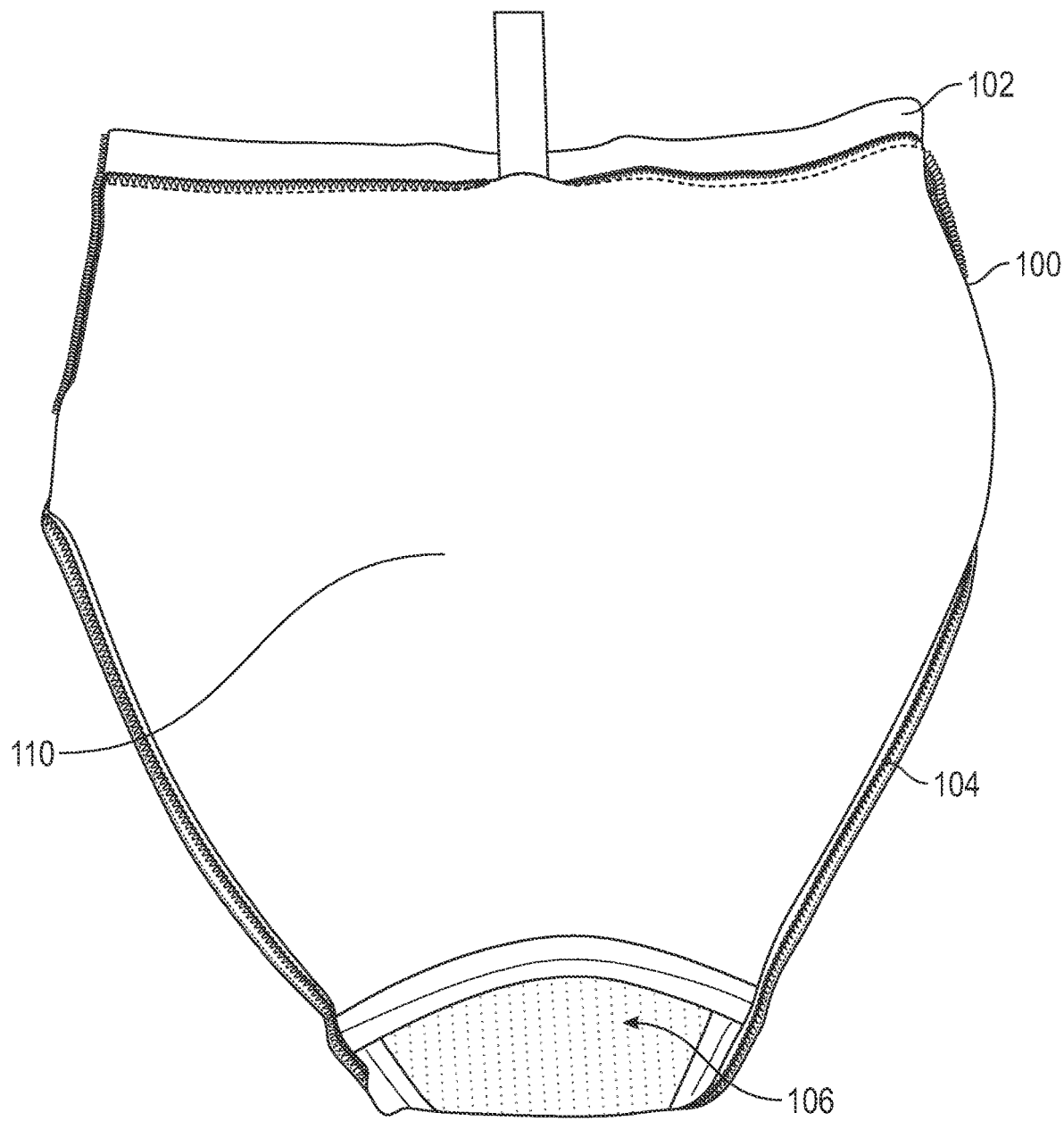

As shown in FIGS. 1 and 2, the underwear or garment 100 includes an external side (distal to wearer's body) having the waistband 102, the front area 108, the back area 110, the pair of leg openings 104, and the crotch area 106. Likewise, as shown in FIGS. 3 and 4, the underwear or garment 100 includes an internal side (proximal to wearer's body) having the waistband 102, the front area 108, the back area 110, the pair of leg openings 104, and the crotch area 106.

As shown in FIGS. 3-8, the crotch area 106 hosts a stitching 112, a first layer 114, a second layer 116, a third layer 118, a fourth layer 120, a fifth layer 122, a sixth layer 124, a seventh layer 126, and a material 128, any of which can include any suitable material or textile (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, tencel). The first layer 114 is innermost. The seventh layer 126 is outermost. Alternatively, the sixth layer 124 is outermost. The second layer 116 extends between the first layer 114 and the third layer 118. The fourth layer 120 extends between the third layer 118 and the fifth layer 122. The sixth layer 124 extends below the fifth layer 122, below the second layer 116, below the first layer 114, and above the seventh layer 126.

The third layer 118 includes a moisture-wicking material (e.g., fabric, natural yarn, synthetic yarn, wool, polypropylene, nylon, polyester). Alternatively, the fourth layer 120 or the fifth layer 122 may include moisture-wicking material. The fourth layer 120 includes an absorbent material (e.g., fabric, natural yarn, synthetic yarn, wool, polypropylene, nylon, polyester). Alternatively, the third layer 118 or the fifth layer 122 includes an absorbent material. The fifth layer 122 includes a waterproof material (can be a coating), but water resistant or water repellant material (can be a coating) can be included as well. Alternatively, the third layer 118 or the fourth layer 120 can include a waterproof material. The second layer 116 includes or comprises a bonding tape (e.g., strip).

As shown in FIG. 8, the stitching 112 extends through the first layer 114, the sixth layer 124, and the seventh layer 126. The stitching 112 avoids extending through the second layer 116, the third layer 118, the fourth layer 120, and the fifth layer 122. The second layer 116 is bonded or adhered to the third layer 118. In certain embodiments, the second layer 116 is bonded or adhered to sixth layer 124. For example, such bonding can be via a suitable bonding tape (e.g., strip). Likewise, for example, such adhering can be via a suitable adhesive (e.g., glue). In certain embodiments, the second layer 116 comprises bonding tape or glue.

In certain embodiments, the edges of at least two of the third layer 118, the fourth layer 120, or the fifth layer 122 are encapsulated via material 128 that extends between the second layer 116 and the sixth layer 124, or between the first layer 114 and the sixth layer 124. The material 128 is U-shaped or C-shaped, but other shapes are possible (e.g., V-shape). The material 128 encapsulates the edges of the third layer 118, the fourth layer 120, and the fifth layer 122, although the material 128 can encapsulate other layers or at least one of the third layer 118, the fourth layer 120, and the fifth layer 122.

In certain embodiments, the material 128 has a first edge and a second edge. In certain embodiments, the first edge of the material is opposite the second edge of the material.

The encapsulation may be achieved, for example, by extending the material 128 from below the fifth layer 122 to above the third layer 118 and around the peripheries of the third layer 118, the fourth layer 120 and the fifth layer 122, and binding the material 128 to an upper portion of the third layer 118 and to a lower portion of the fifth layer 122. The material 128 extends between the second layer 116 and the third layer 118, and between the fifth layer 122 and the sixth layer 124.

In certain embodiments, the second layer 116 is bonded (e.g., bonding tape) or adhered (e.g., adhesive, glue) to the third layer 118 via the material 128. In certain embodiments, bonding tape or glue, other than material 128, is used to bond or adhere the second layer 116 to the third layer. In certain embodiments, the second layer 116 comprises bonding tape or glue and the first layer 114 is coupled to the third layer 118 via the second layer 116.

As shown in FIG. 8, the second layer 116 and the stitching 112 define a gap 132 therebetween. The gap 132 extends between the first layer 114 and the sixth layer 124. The gap 132 can have any volumetric shape. Therefore, since the second layer 116 extends between the first layer 114 and the sixth layer 124 up to a first point 134 and the stitching 112 extends through the first layer 114 and the sixth layer 124 at a second point 136, then the first point 134 is spaced apart from the second point 136 (e.g., between about 0.001 inch and 3 inches).

In certain embodiments, for example, as shown in FIGS. 9, 10, 13, 17 and 18, there is no material 128, and an edge portion 138 of the fifth layer 122 extends beyond the perimeters of the third layer 118 and the fourth layer 120 and over the third layer 118, and is coupled to an upper portion of the third layer 118. In certain embodiments, for example, as shown in FIGS. 9, 10, 17 and 18, the edge portion 138 of the fifth layer 122 is coupled to the upper portion of the third layer 118 and the first layer 114 via the second layer 116.

As shown in FIG. 9, the edge of the second layer 116 extends adjacent or near adjacent to the edges of the first layer 114 and the sixth layer 124 and past the stitching 112, such that the stitching 112 extends through the second layer 116. As shown in FIG. 10, the edge of the second layer 116 does not extend past the stitching 112, such that the stitching 112 extends through the first layer 114 and the sixth layer 124, but not through the second layer 116.

As shown in FIGS. 11 and 12, in certain embodiments, the seventh layer 126 is positioned above the sixth layer 124 which is the outermost layer. The sixth layer 124 includes an edge 140 that extends over the seventh layer 126. The first layer 114 includes an edge 142 that extends and folds under the first layer 114. In certain embodiments the stitching 112 extends through the edge 142 of the first layer 114, the edge 140 of the sixth layer 124, and the seventh layer 126, but not through an outermost portion of the sixth layer 124, or an innermost portion of the first layer 114, to provide a seemingly invisible stitching.

As shown in FIG. 12, in certain embodiments, the first layer 114 includes an edge 142 that folds under the first layer 114, and extends over the second layer 116 towards the third layer 118. In certain embodiments, the edge 142 of the first layer 114 is coupled to the edge 140 of the sixth layer 124 via the second layer 116. As shown in FIG. 11, in certain embodiments, the first layer 114, but not the edge 142 of the first layer 114, is coupled to the sixth layer 124, but not the edge 140 of the sixth layer 124, via the second layer 116. In certain embodiments, the second layer 116 comprises a bonding strip or glue. In certain embodiments the stitching 112 extends through the edge 142 of the first layer 114, the edge 140 of the sixth layer 124, and the seventh layer 126, but not through an innermost portion of the first layer 114 or an outermost portion of the sixth layer 124, to provide a seemingly invisible stitching.

As shown in FIG. 14, in certain embodiments, the first layer 114, and the edge 142 of the first layer 114, is coupled to the sixth layer 124, and the edge 140 of the sixth layer 124, via the second layer 116. In certain embodiments, the second layer 116 comprises a bonding strip or glue. In certain embodiments the stitching 112 extends through the edge 142 of the first layer 114, the second layer 116, the edge 140 of the sixth layer 124, and the seventh layer 126, but not through an innermost portion of the first layer 114 or an outermost portion of the sixth layer 124, to provide a seemingly invisible stitching.

As shown in FIG. 13, the edge portion 138 of the fifth layer 122 is coupled to the third layer 118 via bonding strip or glue 144. The edge of the second layer 116 does not extend past the edge portion 138 in a direction toward the center of the third layer 118, or past the stitching 112 in the other direction, such that the stitching 112 extends through the first layer 114 and the sixth layer 124, but not through the second layer 116. The first layer 114 either extends to the inner edge of the second layer 116 or past the inner edge of the second layer 116. When the first layer 114 extends to the inner edge of the second layer 116, the first layer is coupled to the second layer 116 using bonding strip or glue or the first layer 114 is coupled to the edge 138 of the fifth layer 122 via the second layer 116 which may comprise a bonding strip. When the first layer 114 extends past the inner edge of the second layer 116, the first layer 114 may be coupled to the third layer 118 using a bonding strip or glue and not coupled to the second layer 116, or the first layer 114 may be coupled to both the third layer 118 and the second layer 116 using a bonding strip or glue or a combination of (a) bonding strip or glue and (b) the second layer 116 which may comprise a bonding strip.

As shown in FIGS. 15 and 16, in certain embodiments, similar to the embodiment shown in FIG. 8, the stitching 112 extends through the first layer 114, the sixth layer 124, and the seventh layer 126. The stitching 112 avoids extending through the second layer 116, the third layer 118, the fourth layer 120, and the fifth layer 122. The second layer 116 is bonded or adhered to the third layer 118, but does not extend past the material 128. As shown in FIG. 15, a piece of bonding tape or glue 150 is positioned between the first layer 114 and the sixth layer 124 and couples the first layer 114 to the sixth layer 124, and the stitching 112 passes through the bonding tape or glue 150. In certain embodiments, the second layer 116 comprises bonding tape or glue.

As shown in FIGS. 17 and 18, in certain embodiments, the edge portion 138 of the fifth layer 122 is positioned above the third layer 118 and is coupled to the top of the third layer 118 via the second layer 116. A first edge of the second layer 116 extends over the third layer and couples the first layer 114 to the third layer 118 and the fifth layer 122. A second edge of the second layer 116 does extend past the edge of the fifth layer 122. The stitching 112 extends through the first layer 114 and the sixth layer 124, but not through the second layer 116. As shown in FIG. 17, a piece of bonding tape or glue 150 is positioned between the first layer 114 and the sixth layer 124 and couples the first layer 114 to the sixth layer 124, and the stitching 112 passes through the bonding tape or glue 150. In certain embodiments, the second layer 116 comprises bonding tape or glue.

Figure 19:
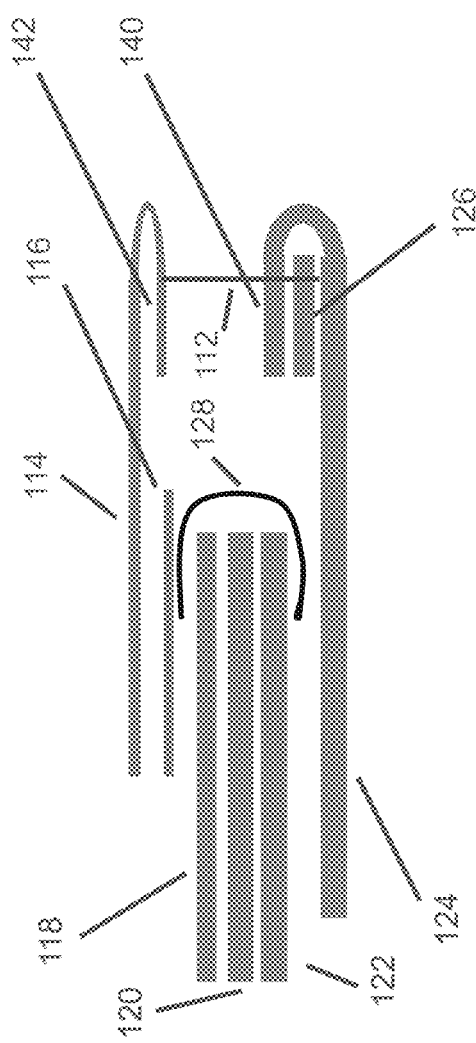
FIG. 19 shows a cross-sectional view of a crotch area of the incontinence and menstrual underwear or garment according to an embodiment of this disclosure.
Figure 20:
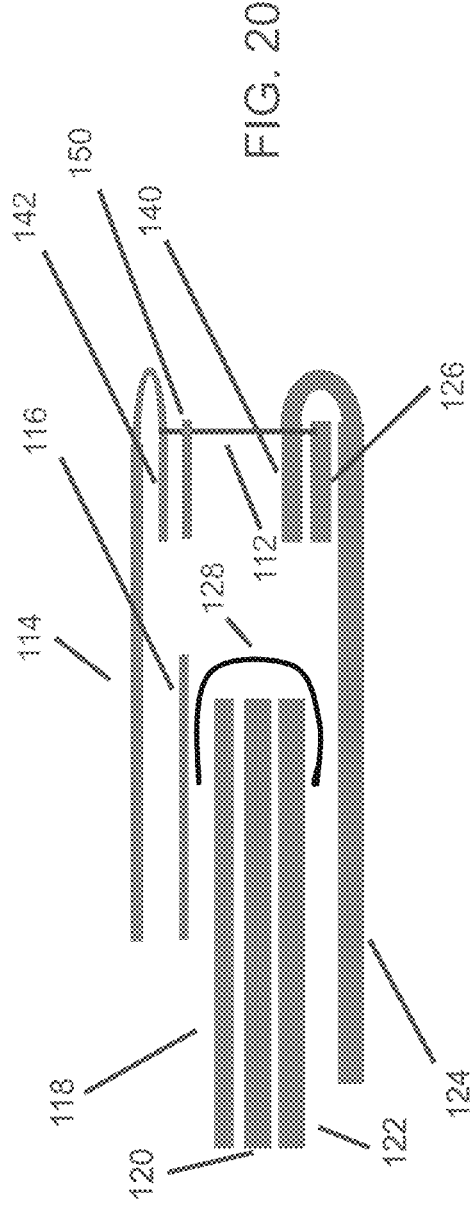
FIG. 20 shows a cross-sectional view of a crotch area of the incontinence and menstrual underwear or garment according to an embodiment of this disclosure.

As shown in FIGS. 19 and 20, in certain embodiments, the seventh layer 126 is positioned above the sixth layer 124 which is the outermost layer. The sixth layer 124 includes an edge 140 that extends over the seventh layer 126. The first layer includes an edge 142 that extends and folds under the first layer 114. In certain embodiments the stitching 112 extends through the edge 142 of the first layer 114, the edge 140 of the sixth layer 124, and the seventh layer 126, but not through an outermost portion of the sixth layer 124, or an innermost portion of the first layer 114, to provide a seemingly invisible stitching.

FIG. 19, in certain embodiments, the second layer does not extend past the edge of the material 128, and only couples a portion of the first layer 114 to the material 128 and the third layer 118. The edge 142 of the first layer 114, is coupled to the edge 140 of the sixth layer 124. In certain embodiments the stitching 112 extends through the edge 142 of the first layer 114, the edge 140 of the sixth layer 124, and the seventh layer 126, but not through an innermost portion of the first layer 114 or an outermost portion of the sixth layer 124, to provide a seemingly invisible stitching. As shown in FIG. 20, a piece of bonding tape or glue 150 is positioned between the edge 142 of the first layer 114 and the edge 140 of the sixth layer 124 and couples the edge 142 of the first layer 114 to the edge 140 of the sixth layer 124, and the stitching 112 passes through the edge 142 of the first layer 114, the bonding tape or glue 150, and the edge 140 of the sixth layer 124. In certain embodiments, the second layer 116 comprises bonding tape or glue.

In certain embodiments, the stitching 112 avoids extending through the material 128. In certain embodiments, for example, as shown in FIGS. 21 and 22, a portion 154 of the material 128 extends in a direction radially to the third layer 118, the fourth layer 120, and the fifth layer 122. In certain embodiments, for example, as shown in FIGS. 21 and 22, a portion 154 of the material 128 is bonded to itself beyond the perimeters of the third layer 118, the fourth layer 120, and the fifth layer 122. The bonding of the material 128 to itself can be accomplished for example, where the material 128 comprises bonding tape, or where glue is placed in a space between layers of the material 128 that comprise the portion 154. In certain embodiments, for example, as shown in FIGS. 21 and 22, the stitching 112 extends through the portion 154 of the material 128 that extends beyond the perimeters of the third layer 118, the fourth layer 120, and the fifth layer 122.

In certain embodiments, such as shown in FIG. 25, the material 128 replaces the second layer 116. In certain embodiments, the material 128 comprises bonding tape or glue. In certain embodiments, for example, as shown in FIGS. 23 and 24, the material 128 replaces a portion of the second layer 116 that extends above the third layer 118. In certain embodiments, for example, as shown in FIGS. 23 and 24, the second layer 116 does not extend between the first layer 114 and the third layer 118. In certain embodiments, for example, as shown in FIGS. 23 and 24, the second layer 116 extends between the first layer 114 and the sixth layer 124. In certain embodiments, for example, as shown in FIGS. 23 and 24, the second layer 116 comprises bonding tape or glue, and the first layer 114 is coupled to the sixth layer 124 via the second layer 116.

In certain embodiments, for example, as shown in FIG. 26, the second layer 116 directly contacts the first layer 114 and the third layer 118. In certain embodiments, for example, as shown in FIG. 27, the second layer 116 directly contacts the first layer 114 and the material 128. In certain embodiments, for example, as shown in FIG. 22, the second layer 116 directly contacts the first layer 114, the third layer 118, and the material 128.

Figure 28:
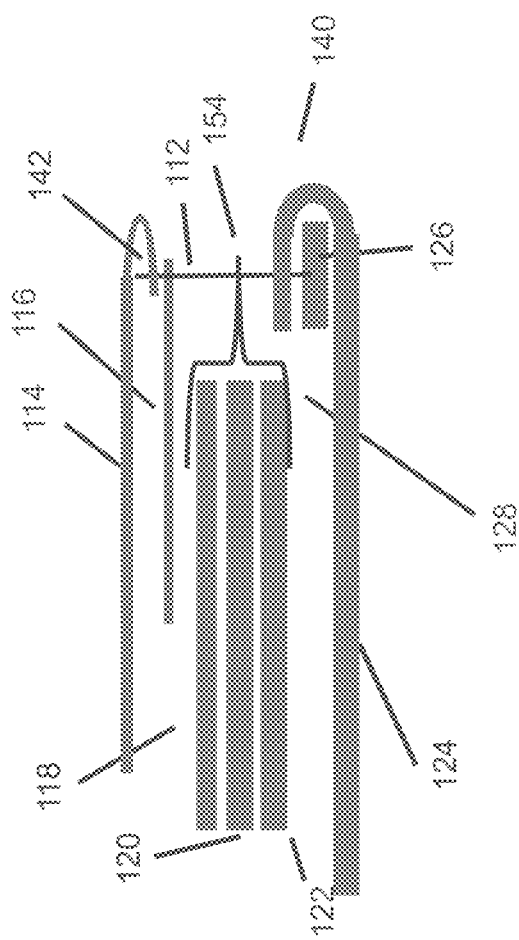
FIG. 28 shows a cross-sectional view of a crotch area of the incontinence and menstrual underwear or garment according to an embodiment of this disclosure.

As shown in FIG. 28, in certain embodiments, the first layer 114, and the edge 142 of the first layer 114, is coupled to the sixth layer 124, and the edge 140 of the sixth layer 124, via the second layer 116. In certain embodiments, the second layer 116 comprises a bonding strip or glue. In certain embodiments the stitching 112 extends through the edge 142 of the first layer 114, the second layer 116, the portion 154 of the material 128 that extends beyond the perimeters of the third layer 118, the fourth layer 120, and the fifth layer 122, the edge 140 of the sixth layer 124, and the seventh layer 126, but not through an innermost portion of the first layer 114 or an outermost portion of the sixth layer 124, to provide a seemingly invisible stitching.

Figure 29:
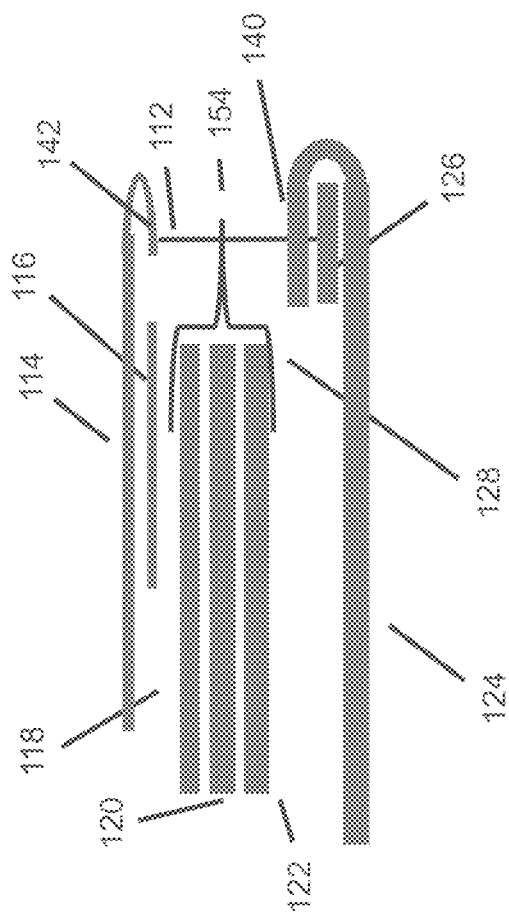
FIG. 29 shows a cross-sectional view of a crotch area of the incontinence and menstrual underwear or garment according to an embodiment of this disclosure.

FIG. 29, in certain embodiments, the second layer does not extend past the edge of the material 128, and only couples a portion of the first layer 114 to the material 128 and the third layer 118. The edge 142 of the first layer 114, is coupled to the edge 140 of the sixth layer 124. In certain embodiments the stitching 112 extends through the edge 142 of the first layer 114, the portion 154 of the material 128 that extends beyond the perimeters of the third layer 118, the fourth layer 120, and the fifth layer 122, the edge 140 of the sixth layer 124, and the seventh layer 126, but not through an innermost portion of the first layer 114 or an outermost portion of the sixth layer 124, to provide a seemingly invisible stitching.

As shown in FIG. 30 and FIG. 31, in certain embodiments, similar to the embodiment shown in FIG. 15, with the addition of a piece of fabric 160 extending from a first edge 162, positioned below the seventh layer 124, to a second edge 164, positioned above first layer 114. The stitching 112 extends through the second edge 164 of the fabric 160, the first layer 114, the sixth layer 126, the seventh layer 124, and the first edge 162 of the fabric 160. The stitching 112 avoids extending through the second layer 116, the third layer 118, the fourth layer 120, and the fifth layer 122. The second layer 116 is bonded or adhered to the third layer 118, but does not extend past the material 128. As shown in FIG. 30, a piece of bonding tape or glue 150 is positioned between the first layer 114 and the sixth layer 126 and couples the first layer 114 to the sixth layer 126, and the stitching 112 also passes through the bonding tape or glue 150. In certain embodiments, the second layer 116 comprises bonding tape or glue.

As shown in FIG. 32, in certain embodiments, a gap can be included between an edge of the second layer 116 and the stitching 112. The method can include extending the gap between the first layer 114 and the sixth layer 124. A piece of fabric 160 extends from a first edge 162, positioned above first layer 114, to a second edge 164, positioned below the seventh layer 124. The stitching 112 extends through the first edge 162 of the fabric 160, the first layer 114, the sixth layer 126, the seventh layer 124, and the second edge 164 of the fabric 160.

In certain embodiments, for example, as shown in FIG. 33, the material 128 replaces a portion of the second layer 116 that extends above the third layer 118, and a piece of fabric 160 extends from a first edge 162, positioned above the first layer 114, to a second edge 164, positioned below the seventh layer 124. The stitching 112 extends through the first edge 162 of the fabric 160, the first layer 114, the sixth layer 126, the seventh layer 124, and the second edge 164 of the fabric 160. In certain embodiments, for example, as shown in FIG. 33, the second layer 116 does not extend between the first layer 114 and the third layer 118. In certain embodiments, for example, as shown in FIG. 33, the second layer 116 extends between the first layer 114 and the sixth layer 126. In certain embodiments, for example, as shown in FIG. 33, the second layer 116 comprises bonding tape or glue, and the first layer 114 is coupled to the sixth layer 126 via the second layer 116.

In certain embodiments, the first layer 114 and the second layer 116 define an elastic edge portion. In certain embodiments, the sixth layer 124 and the seventh layer 126 define an elastic edge portion. For example, the elastic edge portion can include rubber or any other suitable materials (e.g., fabric, natural yarn, synthetic yarn, cotton, silk, polyester, spandex, rubber, plastic, metal, merino wool, nylon, polypropylene, rayon, linen, spandex, bamboo, Gore-Tex, X-static, spandex, tencel).

Figure 5:
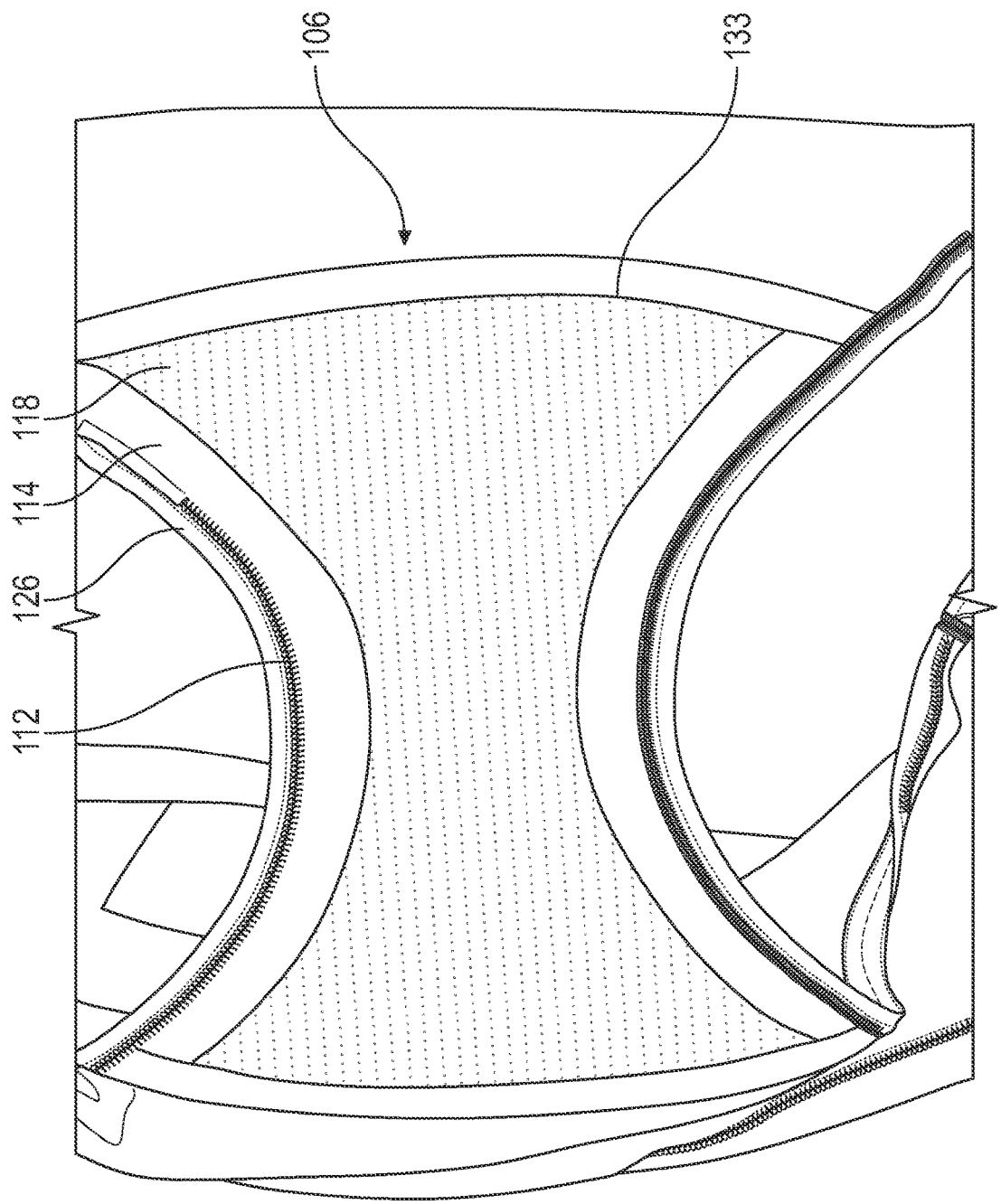
Figure 6:
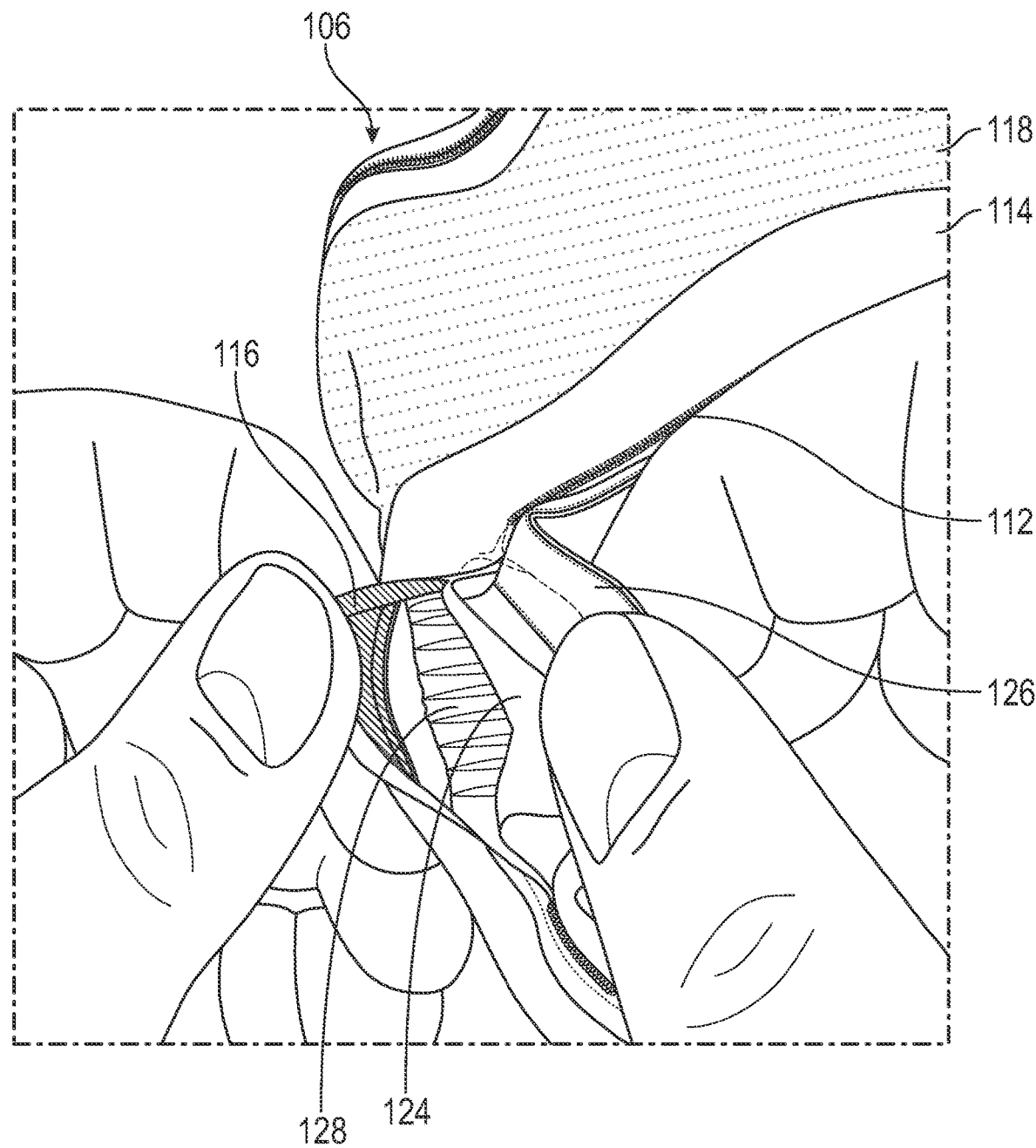
Figure 7:
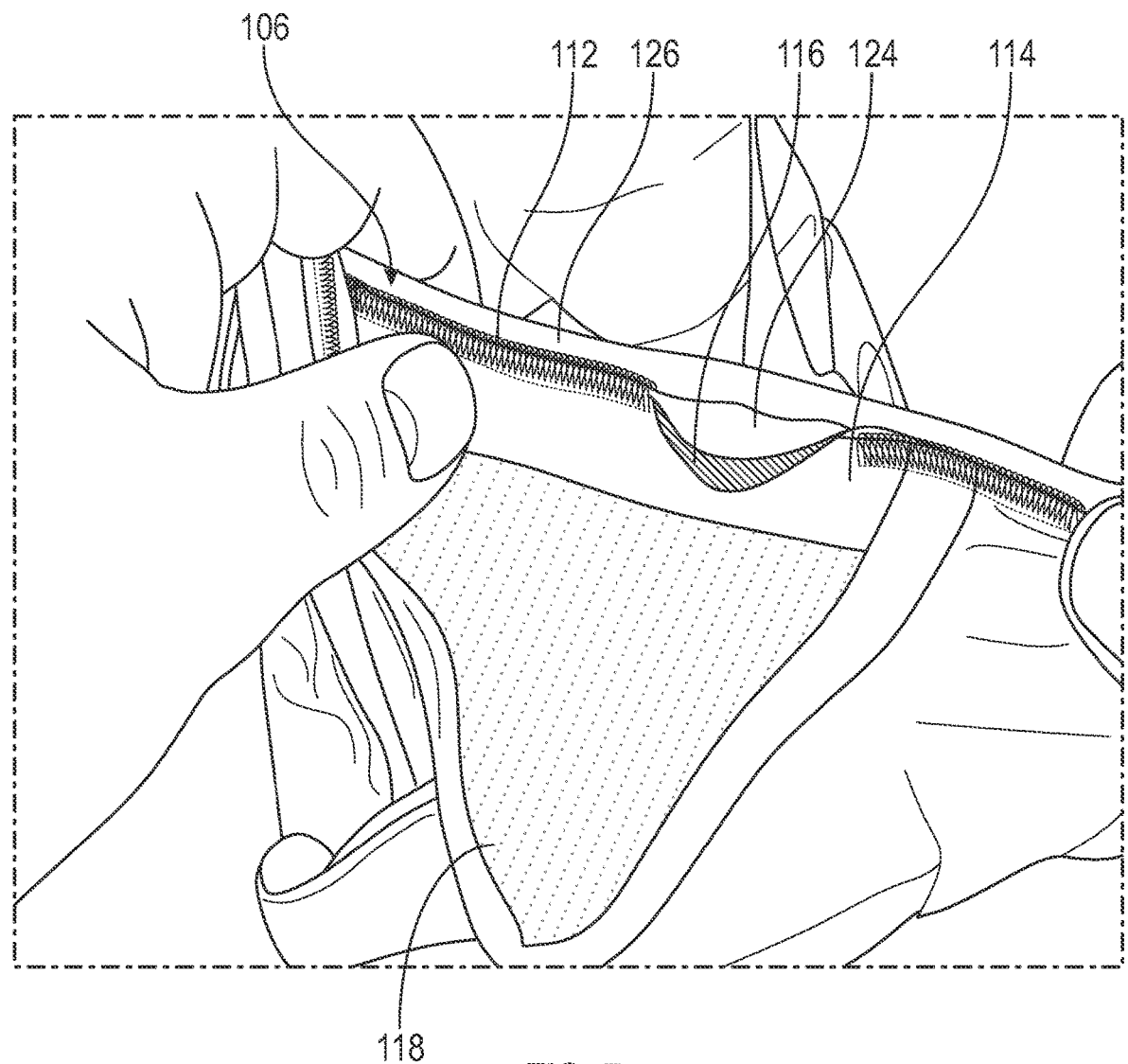

As shown in FIG. 5, the first layer 114 defines a bow shaped area 132 through which the third layer 118 is presented as bow shaped. The third layer 118 is visually distinct relative to the first layer 114, but can avoid being visually distinct. Note that the bow shaped area 132 is not limited to being bow shaped and other shapes or shape patterns are possible (e.g., triangular, circular, rectangular, square, octagon, pentagon, hexagon, pentagonal or hexagonal star, rhombus, polka dot).

In one mode of operation, a method can include: causing the absorptive or incontinence and menstrual underwear or garment 100 to include the crotch area 106 hosting the stitching 112, the first layer 114, the second layer 116, the third layer 118, the fourth layer 120, the fifth layer 122, the sixth layer 124, and the seventh layer 126 and a material 128. The first layer 114 is innermost and the seventh layer 126 is outermost. Alternatively, the sixth layer 124 is outermost. The method can include causing the second layer 116 to extend between the first layer 114 and the third layer 118 such that the second layer 116 is bonded or adhered to the third layer 118. The method can include causing the fourth layer 120 to extend between the third layer 118 and the fifth layer 122. The method can include causing the sixth layer 124 to extend below the fifth layer 122, below the second layer 116, below the first layer 114, and above the seventh layer 126. The method can include causing the stitching 112 to extend through the first layer 114, the second layer 116, the sixth layer 124, and the seventh layer 126 and avoid extending through the third layer 118, the fourth layer 120, and the fifth layer 122.

In one mode of operation, the third layer 118 wicks moisture (e.g., fabric, natural yarn, synthetic yarn, wool, polypropylene, nylon, polyester). Alternatively, the fourth layer 120 or the fifth layer 122 may wick moisture. The fourth layer 120 absorbs moisture (e.g., fabric, natural yarn, synthetic yarn, wool, polypropylene, nylon, polyester). Alternatively, the third layer 118 or the fifth layer 122 absorb moisture. The fifth layer 122 prevents transfer of moisture (can be a coating). Alternatively, the third layer 118 or the fourth layer 120 prevent transfer of moisture. The second layer 116 includes or comprises a bonding tape (e.g., strip).

According to one mode of operation, as shown in FIG. 8, the method can include causing the stitching 112 to extend through the first layer 114, the sixth layer 124, and the seventh layer 126. According to one mode of operation, the method can include avoiding the stitching 112 from extending through the second layer 116, the third layer 118, the fourth layer 120, and the fifth layer 122. The second layer 116 is bonded or adhered to the third layer 118. In certain embodiments, the method can include bonding or adhering the second layer 116 to the sixth layer 124. For example, such bonding can be via a suitable bonding tape (e.g., strip). Likewise, for example, such adhering can be via a suitable adhesive (e.g., glue).

In certain embodiments, the method can include bonding or adhering the second layer 116 to the third layer 118 via the material 128. In certain embodiments, the method can include bonding or adhering the second layer 116 to the sixth layer 124. For example, such bonding can be via a suitable bonding tape (e.g., strip). Likewise, for example, such adhering can be via a suitable adhesive (e.g., glue). In certain embodiments, bonding tape or glue, other than material 128, is used to bond or adhere the second layer 116 to the third layer. In certain embodiments, the second layer 116 comprises bonding tape or glue and the first layer 114 is coupled to the third layer 118 via the second layer 116.

In certain embodiments, the method can include encapsulating at least two of the third layer 118, the fourth layer 120, or the fifth layer 120 via material 128 that extends between the second layer 116 and the sixth layer 124 or between the first layer 114 and the sixth layer 124. The material 128 is U-shaped or C-shaped, but other shapes are possible (e.g., V-shape). The method can include material 128 encapsulating the edges of the third layer 118, the fourth layer 120, and the fifth layer 122, although the material 128 can encapsulate other layers or at least one of the third layer 118, the fourth layer 120, and the fifth layer 122.

The encapsulation may be achieved, for example, by extending the material 128 from below the fifth layer 122 to above the third layer 118 and around the periphery of the third layer 118, the fourth layer 120 and the fifth layer 122, and binding the material 128 to an upper portion of the third layer 118 and to a lower portion of the fifth layer 122. The material 128 extends between the second layer 116 and the third layer 118, and between the fifth layer 122 and the sixth layer 124.

As shown in FIG. 9, in certain embodiments, the method can include extending the edge of the second layer 116 adjacent or near adjacent to the edges of the first layer 114 and the sixth layer 124 and past the stitching 112, such that the stitching 112 is extended through the second layer 116. As shown in FIG. 10, in certain embodiments, the method can include not extending the edge of the second layer 116 past the stitching 112, such that the stitching 112 is extended through the first layer 114 and the sixth layer 124, but not through the second layer 116.

As shown in FIGS. 11 and 12, in certain embodiments, the method can include positioning the seventh layer 126 above the sixth layer 124 which is the outermost layer. The sixth layer 124 includes an edge 140 that is extended over the seventh layer 126. The first layer 114 includes an edge 142 that is extended and folded under the first layer 114. In certain embodiments, the method can include extending the stitching 112 through the edge 142 of the first layer 114, the edge 140 of the sixth layer 124, and the seventh layer 126, but not through an outermost portion of the sixth layer 124, or an innermost portion of the first layer 114, to provide a seemingly invisible stitching.

As shown in FIG. 12, in certain embodiments, the method can include folding an edge 142 of the first layer 114 under the first layer 114, and extending the edge 142 over the second layer 116 towards the third layer 118. In certain embodiments, the method can include coupling the edge 142 of the first layer 114 to the edge 140 of the sixth layer 124 via the second layer 116. As shown in FIG. 11, in certain embodiments, the method can include coupling the first layer 114, but not the edge 142 of the first layer 114, to the sixth layer 124, but not the edge 140 of the sixth layer 124, via the second layer 116. In certain embodiments, the second layer 116 comprises a bonding strip or glue. In certain embodiments, the method can include extending the stitching 112 extends the edge 142 of the first layer 114, the edge 140 of the sixth layer 124, and the seventh layer 126, but not through an innermost portion of the first layer 114 or an outermost portion of the sixth layer 124, to provide a seemingly invisible stitching.

As shown in FIG. 14, in certain embodiments, the method can include coupling the first layer 114, and the edge 142 of the first layer 114, to the sixth layer 124, and the edge 140 of the sixth layer 124, via the second layer 116. In certain embodiments, the second layer 116 comprises a bonding strip or glue. In certain embodiments, the method can include extending the stitching 112 through the edge 142 of the first layer 114, the second layer 116, the edge 140 of the sixth layer 124, and the seventh layer 126, but not through an innermost portion of the first layer 114 or an outermost portion of the sixth layer 124, to provide a seemingly invisible stitching.

As shown in FIG. 13, in certain embodiments, the method can include coupling the edge portion 138 of the fifth layer 122 to the third layer 118 via a bonding strip or glue 144. In certain embodiments, the method can include not extending the edge of the second layer 116 past the edge portion 138 in a direction toward the center of the third layer 118, or past the stitching 112 in the other direction, such that the stitching 112 is extended through the first layer 114 and the sixth layer 124, but not through the second layer 116. In certain embodiments, the method can include extending the first layer 114 to the inner edge of the second layer 116 or past the inner edge of the second layer 116. When the first layer 114 is extended to the inner edge of the second layer 116, the first layer is coupled to the second layer 116 using bonding strip or glue or the first layer 114 is coupled to the edge 138 of the fifth layer 122 via the second layer 116 which may comprise a bonding strip. When the first layer 114 is extended past the inner edge of the second layer 116, the first layer 114 may be coupled to the third layer 118 using a bonding strip or glue and not coupled to the second layer 116, or the first layer 114 may be coupled to both the third layer 118 and the second layer 116 using a bonding strip or glue or a combination of (a) bonding strip or glue and (b) the second layer 116 which may comprise a bonding strip.

As shown in FIGS. 15 and 16, in certain embodiments, similar to the embodiment shown in FIG. 8, the method can include extending the stitching 112 through the first layer 114, the sixth layer 124, and the seventh layer 126. In certain embodiments, the method can include avoiding extending the stitching 112 through the second layer 116, the third layer 118, the fourth layer 120, and the fifth layer 122. In certain embodiments, the method can include bonding or adhering the second layer 116 to the third layer 118, not extending second layer past the material 128. As shown in FIG. 15, in certain embodiments, the method can include positioning a piece of bonding tape or glue 150 between the first layer 114 and the sixth layer 124 and coupling the first layer 114 to the sixth layer 124, and passing the stitching 112 through the bonding tape or glue 150. In certain embodiments, the second layer 116 comprises bonding tape or glue.

As shown in FIGS. 17 and 18, in certain embodiments, the method can include positioning the edge portion 138 of the fifth layer 122 above the third layer 118 and coupling it to the top of the third layer 118 via the second layer 116. In certain embodiments, the method can include extending a first edge of the second layer 116 over the third layer and coupling the first layer 114 to the third layer 118 and the fifth layer 122. In certain embodiments, the method can include not extending a second edge of the second layer 116 past the edge of the fifth layer 122. In certain embodiments, the method can include extending the stitching 112 through the first layer 114 and the sixth layer 124, but not through the second layer 116. As shown in FIG. 17, in certain embodiments, the method can include positioning a piece of bonding tape or glue 150 between the first layer 114 and the sixth layer 124 and coupling it the first layer 114 to the sixth layer 124, and passing the stitching 112 through the bonding tape or glue 150. In certain embodiments, the second layer 116 comprises bonding tape or glue.

As shown in FIGS. 19 and 20, in certain embodiments, the method can include positioning the seventh layer 126 above the sixth layer 124 which is the outermost layer. In certain embodiments, the method can include extending an edge 140 of the sixth layer 124 over the seventh layer 126. In certain embodiments, the method can include extending an edge 142 of the first layer and folding the edge 142 under the first layer 114. In certain embodiments, the method can include extending the stitching 112 through the edge 142 of the first layer 114, the edge 140 of the sixth layer 124, and the seventh layer 126, but not through an outermost portion of the sixth layer 124, or an innermost portion of the first layer 114, to provide a seemingly invisible stitching.

FIG. 19, in certain embodiments, the method can include not extending the second layer past the edge of the material 128, and only coupling a portion of the first layer 114 to the material 128 and the third layer 118. In certain embodiments, the method can include coupling the edge 142 of the first layer 114, to the edge 140 of the sixth layer 124. In certain embodiments, the method can include extending the stitching 112 through the edge 142 of the first layer 114, the edge 140 of the sixth layer 124, and the seventh layer 126, but not through an innermost portion of the first layer 114 or an outermost portion of the sixth layer 124, to provide a seemingly invisible stitching. As shown in FIG. 20, In certain embodiments, the method can include positioning a piece of bonding tape or glue 150 between the edge 142 of the first layer 114 and the edge 140 of the sixth layer 124 and coupling the edge 142 of the first layer 114 to the edge 140 of the sixth layer 124, and passing the stitching 112 through the edge 142 of the first layer 114, the bonding tape or glue 150, and the edge 140 of the sixth layer 124. In certain embodiments, the second layer 116 comprises bonding tape or glue.

In certain embodiments, the method can include avoiding extending the stitching 112 through the material 128. In certain embodiments, the method can include for example, as shown in FIGS. 21 and 22, extending a portion 154 of the material 128 in a direction radially to the third layer 118, the fourth layer 120, and the fifth layer 122. In certain embodiments, the method can include for example, as shown in FIGS. 21 and 22, bonding a portion 154 of the material 128 to itself beyond the perimeters of the third layer 118, the fourth layer 120, and the fifth layer 122. In certain embodiments, the method can include bonding of the material 128 to itself, where the material 128 comprises bonding tape, or where glue is placed in a space between layers of the material 128 that comprise the portion 154. In certain embodiments, the method can include for example, as shown in FIGS. 21 and 22, extending the stitching 112 through the portion 154 of the material 128 that extends beyond the perimeters of the third layer 118, the fourth layer 120, and the fifth layer 122.

In certain embodiments, such as shown in FIG. 25, the method can include replacing the second layer 116 with the material 128. In certain embodiments, the material 128 comprises bonding tape or glue. In certain embodiments, the method can include for example, as shown in FIGS. 23 and 24, replacing a portion of the second layer 116 that extends above the third layer 118 with the material 128. In certain embodiments, the method can include for example, as shown in FIGS. 23 and 24, not extending the second layer 116 between the first layer 114 and the third layer 118. In certain embodiments, the method can include for example, as shown in FIGS. 23 and 24, extending the second layer 116 between the first layer 114 and the sixth layer 124. In certain embodiments, the method can include for example, as shown in FIGS. 23 and 24, where the second layer 116 comprises bonding tape or glue, coupling the first layer 114 to the sixth layer 124 via the second layer 116.

In certain embodiments, the method can include for example, as shown in FIG. 26, directly contacting the second layer 116 to the first layer 114 and the third layer 118. In certain embodiments, the method can include for example, as shown in FIG. 27, directly contacting the second layer 116 to the first layer 114 and the material 128. In certain embodiments, the method can include for example, as shown in FIG. 22, directly contacting the second layer 116 to the first layer 114, the third layer 118, and the material 128.

As shown in FIG. 28, in certain embodiments, the method can include coupling the first layer 114, and the edge 142 of the first layer 114, to the sixth layer 124, and the edge 140 of the sixth layer 124, via the second layer 116. In certain embodiments, the method can include the second layer 116 comprises a bonding strip or glue. In certain embodiments, the method can include extending the stitching 112 through the edge 142 of the first layer 114, the second layer 116, the portion 154 of the material 128 that extends beyond the perimeters of the third layer 118, the fourth layer 120, and the fifth layer 122, the edge 140 of the sixth layer 124, and the seventh layer 126, but not through an innermost portion of the first layer 114 or an outermost portion of the sixth layer 124, to provide a seemingly invisible stitching.

As shown in FIG. 29, in certain embodiments, the method can include not extending the second layer past the edge of the material 128, and only coupling a portion of the first layer 114 to the material 128 and the third layer 118. In certain embodiments, the method can include coupling the edge 142 of the first layer 114, to the edge 140 of the sixth layer 124. In certain embodiments, the method can include extending the stitching 112 through the edge 142 of the first layer 114, the portion 154 of the material 128 that extends beyond the perimeters of the third layer 118, the fourth layer 120, and the fifth layer 122, the edge 140 of the sixth layer 124, and the seventh layer 126, but not through an innermost portion of the first layer 114 or an outermost portion of the sixth layer 124, to provide a seemingly invisible stitching.

As shown in FIG. 30 and FIG. 31, in certain embodiments, the method can include, similar to the embodiment shown in FIG. 15, positioning a first edge 162 of a piece of fabric 160 above first layer 114 and extending a second edge 164 of the piece of fabric to a position below the seventh layer 124. In certain embodiments, the method can include extending the stitching 112 through the first edge 162 of the fabric 160, the first layer 114, the sixth layer 126, the seventh layer 124, and the second edge 164 of the fabric 160. In certain embodiments, the method can include avoiding extending the stitching 112 through the second layer 116, the third layer 118, the fourth layer 120, and the fifth layer 122. In certain embodiments, the method can include bonding or adhering the second layer 116 to the third layer 118, but not extending the second layer past the material 128. As shown in FIG. 30, in certain embodiments, the method can include positioning a piece of bonding tape or glue 150 between the first layer 114 and the sixth layer 126 and coupling the first layer 114 to the sixth layer 126, and passing the stitching 112 through the bonding tape or glue 150. In certain embodiments, the second layer 116 comprises bonding tape or glue.

As shown in FIG. 32, in certain embodiments, the method can include providing a gap between an edge of the second layer 116 and the stitching 112. In certain embodiments, the method can include extending the gap between the first layer 114 and the sixth layer 124. In certain embodiments, the method can include positioning a first edge 162 of a piece of fabric 160 above the first layer 114 and extending a second edge 164 of the piece of fabric 160 to a position below the seventh layer 124. In certain embodiments, the method can include extending the stitching 112 through the upper edge of the fabric 160, the first layer 114, the sixth layer 126, the seventh layer 124, and the bottom edge of the fabric 160.

In certain embodiments, for example, as shown in FIG. 33, the method can include replacing a portion of the second layer 116 that extends above the third layer 118 with the material 128, and positioning a first edge 162 of a piece of fabric 160 above the first layer 114 and extending a second edge 164 of the piece of fabric 160 to a position below the seventh layer 124. In certain embodiments, the method can include extending the stitching 112 through the first edge 162 of the fabric 160, the first layer 114, the sixth layer 126, the seventh layer 124, and the second edge 164 of the fabric 160. In certain embodiments, for example, as shown in FIG. 33, the method can include not extending the second layer 116 between the first layer 114 and the third layer 118. In certain embodiments, for example, as shown in FIG. 33, the method can include extending the second layer 116 between the first layer 114 and the sixth layer 126. In certain embodiments, for example, as shown in FIG. 33, the method can include the second layer 116 comprising bonding tape or glue, and coupling the first layer 114 to the sixth layer 126 via the second layer 116.

In certain embodiments, the method can include bonding (e.g., bonding tape) or adhering (e.g., adhesive, glue) the second layer 116 to the third layer 118 via the material 128. In certain embodiments, bonding tape or glue, other than material 128, is used to bond or adhere the second layer 116 to the third layer. In certain embodiments, the second layer 116 comprises bonding tape or glue and coupling the first layer 114 to the third layer 118 via the second layer 116. In certain embodiments, such as shown in FIG. 25, the material 128 replaces the second layer 116. In certain embodiments, the material 128 comprises bonding tape or glue. In certain embodiments, for example, as shown in FIGS. 23 and 24, the material 128 replaces a portion of the second layer 116 that extends above the third layer 118. In certain embodiments, for example, as shown in FIGS. 23 and 24, the second layer 116 does not extend between the first layer 114 and the third layer 118. In certain embodiments, for example, as shown in FIGS. 23 and 24, the second layer 116 extends between the first layer 114 and the sixth layer 124. In certain embodiments, for example, as shown in FIGS. 23 and 24, the second layer 116 comprises bonding tape or glue, and the first layer 114 is coupled to the sixth layer 124 via the second layer 116.

In certain embodiments, the method can include avoiding extending the stitching 112 through the material 128. In certain embodiments, for example, as shown in FIGS. 21 and 22, a portion 154 of the material 128 is extended beyond the perimeters of and in a direction radially to the third layer 118, the fourth layer 120, and the fifth layer 122. In certain embodiments, for example, as shown in FIGS. 21 and 22, a portion 154 of the material 128 is bonded to itself beyond the perimeters of the third layer 118, the fourth layer 120, and the fifth layer 122. The bonding of the material 128 to itself can be accomplished for example, where the material 128 comprises bonding tape, or where glue is placed in a space between layers of the material 128 that comprise the portion 154. In certain embodiments, for example, as shown in FIGS. 21 and 22, the stitching 112 is extended through the portion 154 of the material 128 that extends beyond the perimeters of the third layer 118, the fourth layer 120, and the fifth layer 122.

In certain embodiments, for example, as shown in FIGS. 9, 10, 13, 17 and 18, the method can include not using material 128, and extending an edge portion 138 of the fifth layer 122 beyond the perimeters of the third layer 118 and the fourth layer 120 and over the third layer 118, and coupling the edge portion 138 of the fifth layer 122 to an upper portion of the third layer 118. In certain embodiments, for example, as shown in FIGS. 9, 10, 17 and 18, the method can include coupling the edge portion 138 of the fifth layer 122 to the upper portion of the third layer 118 and the first layer 114 via the second layer 116.

In some embodiments, the absorptive or incontinence and menstrual underwear or garment 100 can be embodied as disclosed in US20160089276, EP2879534, US20180014983, US20180092787, JP3718213, all of which are incorporated by reference herein for all purposes. As such, any of such references can be modified based on this disclosure using various principles, as known to skilled artisans in this technical field.

In some embodiments, various functions or acts can take place at a given location and/or in connection with the operation of one or more apparatuses or systems. In some embodiments, a portion of a given function or act can be performed at a first device or location, and a remainder of the function or act can be performed at one or more additional devices or locations.

The corresponding structures, materials, acts, and equivalents of all means or step plus function elements in the claims below are intended to include any structure, material, or act for performing the function in combination with other claimed elements as specifically claimed. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the steps can be performed in a differing order or steps can be added, deleted or modified. All of these variations are considered a part of the disclosure. It will be understood that those skilled in the art, both now and in the future, can make various improvements and enhancements which fall within the scope of the claims which follow.

The description of this disclosure has been presented for purposes of illustration and description, but is not intended to be fully exhaustive and/or limited to the disclosure in the form disclosed. Many modifications and variations in techniques and structures will be apparent to those of ordinary skill in an art without departing from a scope and spirit of this disclosure as set forth in the claims that follow. Accordingly, such modifications and variations are contemplated as being a part of this disclosure. A scope of this disclosure is defined by various claims, which include known equivalents and unforeseeable equivalents at a time of filing of this disclosure.

What is claimed is:

1. A device comprising:
an absorptive garment including a crotch area hosting a stitching, a first layer, a second layer, a third layer, a fourth layer, a fifth layer, a sixth layer, and a seventh layer, wherein the first layer is innermost, wherein at least one of the sixth layer or the seventh layer is outermost, wherein the first layer extends along the second layer, wherein the first layer extends beyond a peripheral edge of at least one of the second layer or the third layer, wherein the first layer does not extend over a central portion of the third layer, wherein the second layer extends along a peripheral portion of the third layer, wherein the second layer does not extend over a central portion of the third layer, wherein the second layer extends between the first layer and the third layer, wherein the fourth layer extends between the third layer and the fifth layer, wherein the sixth layer extends below the fifth layer and at least one of above or below the seventh layer, wherein the stitching extends through the first layer, the sixth layer, and the seventh layer, wherein the stitching avoids extending through the second layer, the third layer, the fourth layer, and the fifth layer, wherein the second layer is bonded or adhered to the third layer.

2. The device of claim 1, wherein the first layer is bonded or adhered to the sixth layer.

3. The device of claim 1, wherein the third layer, the fourth layer, or the fifth layer includes a moisture-wicking material.

4. The device of claim 1, wherein the third layer, the fourth layer, or the fifth layer includes a waterproof material.

5. The device of claim 1, wherein the second layer includes a bonding tape.

6. The device of claim 1, wherein the second layer is bonded to the sixth layer.

7. The device of claim 1, wherein at least two of the peripheries of the third layer, the fourth layer, or the fifth layer are surrounded via a material having a first edge and a second edge opposite the first edge, wherein the material extends from the first edge positioned between the second layer and the third layer to the second edge positioned between the fifth layer and the sixth layer.

8. The device of claim 7, wherein the second layer directly contacts the first layer and a material overlaying the third layer.

9. The device of claim 1, further comprising an extension of the second layer, wherein the second layer extends between the first layer and the third layer at a first point, wherein the stitching extends through the second layer at a second point, and wherein the first point is spaced apart from the second point.

10. The device of claim 1, wherein at least one of (i) the first layer and the second layer (ii) the sixth layer and the seventh layer, or (iii) the first layer, the second layer, the sixth layer, and the seventh layer define an elastic edge portion.

11. The device of claim 1, wherein the first layer defines a bow shaped area through which the third layer is presented as bow shaped.

12. The device of claim 1, wherein the third layer is visually distinct relative to the first layer.

13. The device of claim 1, wherein the second layer directly contacts the first layer and the third layer.

14. The device of claim 1, wherein the fifth layer overlays the third layer and the peripheries of the third layer and the fourth layer.

15. The device of claim 14, wherein the fifth layer extends from below the fourth layer to above the third layer and below the second layer, and the fifth layer is bonded to the third layer.

16. The device of claim 15, wherein the fifth layer is bonded or adhered to the second layer.

17. The device of claim 14, wherein the second layer does not extend past the fifth layer.

18. The device of claim 1, wherein the absorptive garment is at least one of an incontinence garment, a menstrual garment, or an incontinence and menstrual garment.

19. The device of claim 1, wherein at least two of the peripheries of the third layer, the fourth layer, or the fifth layer are surrounded via a material having a first edge and a second edge opposite the first edge, wherein the material extends from the first edge positioned between the first layer and the third layer to the second edge positioned between the fifth layer and the sixth layer, and wherein the second layer does not extend over the first edge.

20. The device of claim 1, wherein at least two of the peripheries of the third layer, the fourth layer, or the fifth layer are surrounded via a material having a first edge and a second edge opposite the first edge wherein the material extends from the first edge positioned between the first layer and the third layer to the second edge positioned between the fifth layer and the sixth layer, wherein the material has a U-shaped, a C-shaped, or a V-shaped cross-section, and includes a portion of the material that extends from the apex opposite the opening of the U, the C, or V past the stitching, wherein the stitching extends through the piece of the material, and wherein the second layer does not extend over the first edge.

21. An absorptive garment including a crotch area hosting a stitching, a first layer, a second layer, a third layer, a fourth layer, a fifth layer, a sixth layer, and a seventh layer, wherein the first layer is innermost, wherein at least one of the sixth layer or the seventh layer is outermost, wherein the second layer extends between the first layer and the third layer, wherein the fourth layer extends between the third layer and the fifth layer, wherein the sixth layer extends below the fifth layer and at least one of above or below the seventh layer, wherein the stitching extends through the first layer, the sixth layer, and the seventh layer, wherein the stitching avoids extending through the second layer, the third layer, the fourth layer, and the fifth layer, wherein the second layer is bonded or adhered to the third layer, wherein at least two of the peripheries of the third layer, the fourth layer, or the fifth layer are surrounded via a material having a first edge and a second edge opposite the first edge, wherein the material extends from the first edge positioned between the second layer and the third layer to the second edge positioned between the fifth layer and the sixth layer, wherein the material has a U-shaped, a C-shaped, or a V-shaped cross-section, and includes a portion of the material that extends from the apex opposite the opening of the U, the C, or V past the stitching, wherein the stitching extends through the piece of the material.

22. The device of claim 21, wherein the second layer at least one of (i) does not extend past the apex of the material, or (ii) does not extend over the material.

23. The device of claim 21, further comprising an extension of the second layer, wherein the stitching extends through the second layer.

24. The device of claim 21, wherein the second layer extends only over the material and does not extend past the apex of the material.

25. The device of claim 21, wherein the seventh layer is positioned above the sixth layer, an edge of the sixth layer extends below the seventh layer and past an edge of the seventh layer in a direction toward the first layer and over the seventh layer, and an edge of the first layer extends below the first layer.

26. The device of claim 25, wherein the second layer does not extend past the apex of the material.

27. The device of claim 25, wherein the stitching extends through the edge of the first layer, the edge of the sixth layer and the seventh layer, but not through the innermost portion of the first layer or the outermost portion of the sixth layer.

28. The device of claim 27, further comprising an extension of the second layer, wherein the stitching extends through the second layer.

29. A device comprising:
an absorptive garment including a crotch area hosting a stitching, a first layer, a second layer, a third layer, a fourth layer, a fifth layer, a sixth layer, and a seventh layer, wherein the first layer is innermost, wherein at least one of the sixth layer or the seventh layer is outermost, wherein the first layer extends along the second layer, wherein the first layer extends beyond a peripheral edge of at least one of the second layer or the third layer, wherein the first layer does not extend over a central portion of the third layer, wherein the second layer extends along a peripheral portion of the third layer, wherein the second layer does not extend over a central portion of the third layer, wherein the second layer extends below the first layer, wherein the fourth layer extends between the third layer and the fifth layer, wherein the sixth layer extends below the fifth layer and at least one of above or below the seventh layer, wherein at least two of the peripheries of the third layer, the fourth layer, or the fifth layer are surrounded via a material having a first edge and a second edge opposite the first edge, wherein the material extends from the first edge positioned between the second layer and the third layer to the second edge positioned between the fifth layer and the sixth layer, wherein the stitching extends through the first layer, the sixth layer, and the seventh layer, wherein the stitching avoids extending through the second layer, the third layer, the fourth layer, the fifth layer, and the material, and wherein the second layer is bonded or adhered to the third layer.

30. A method comprising:
causing an absorptive garment to include a crotch area hosting a stitching, a first layer, a second layer, a third layer, a fourth layer, a fifth layer, a sixth layer, and a seventh layer, wherein the first layer is innermost, wherein at least one of the sixth layer or the seventh layer is outermost;
causing the first layer to extend along the second layer;
causing the first layer to extend beyond a peripheral edge of at least one of the second layer or the third layer;
causing the first layer to not extend over a central portion of the third layer;
causing the second layer to extend along a peripheral portion of the third layer;
causing the second layer to not extend over a central portion of the third layer;
causing the second layer to extend between the first layer and the third layer such that the second layer is bonded or adhered to the third layer;
causing the fourth layer to extend between the third layer and the fifth layer;
causing the sixth layer to extend between the fifth layer and at least one of above or below the seventh layer;
causing the stitching to extend through the first layer, the sixth layer, and the seventh layer and avoid extending through the second layer, the third layer, the fourth layer, and the fifth layer; and
bonding or adhering the second layer to the third layer.

* * * * *